United States Patent
Takano et al.

(10) Patent No.: US 6,562,839 B1
(45) Date of Patent: May 13, 2003

(54) 6-SUBSTITUTED HETEROQUINOLINECARBOXYLIC ACID DERIVATIVES AND ADDITION SALTS THEREOF AND PROCESSES FOR THE PREPARATION OF BOTH

(75) Inventors: Yasuo Takano, Kazo; Jun Asano, Sugito-machi; Tsuyoshi Anraku, Koga; Kazunori Fukuchi, Hanyu, all of (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/926,054

(22) PCT Filed: Feb. 25, 2000

(86) PCT No.: PCT/JP00/01077
§ 371 (c)(1),
(2), (4) Date: Aug. 22, 2001

(87) PCT Pub. No.: WO00/50416
PCT Pub. Date: Aug. 31, 2000

(30) Foreign Application Priority Data

Feb. 26, 1999 (JP) .............................. 11-050239
Feb. 18, 2000 (JP) ........................ 2000-041814

(51) Int. Cl.⁷ ...................... A61K 31/47; C07D 215/16; C07D 215/20
(52) U.S. Cl. ........................ 514/312; 546/156; 546/157; 546/158
(58) Field of Search ................ 546/156, 157, 546/158; 514/312

(56) References Cited

U.S. PATENT DOCUMENTS

| 5,252,584 A | 10/1993 | Carling et al. |
| 5,475,008 A | 12/1995 | Carling et al. |
| 5,607,928 A | * 3/1997 | Arnould |

FOREIGN PATENT DOCUMENTS

| CA | 2056808 | 6/1992 |
| DE | DE 43 40 045 A1 | 6/1998 |
| EP | 0 489 4 58 | 6/1992 |
| EP | 0489458 | * 6/1992 |
| FR | EP 0 640 612 A1 | 3/1995 |
| FR | EP 0 818 449 A1 | 1/1998 |
| JP | 6-9618 | 1/1994 |
| JP | 7-501313 | 2/1995 |
| JP | 2000-80085 | 3/2000 |
| WO | WO 93/10783 | 6/1993 |
| WO | 93/10783 | * 6/1993 |
| WO | WO 97/49701 | 12/1997 |
| WO | 99/11632 | * 3/1999 |
| WO | WO 99/11632 | 3/1999 |

* cited by examiner

*Primary Examiner*—D. Margaret Seaman
(74) *Attorney, Agent, or Firm*—Oblon, Spivak, McClelland, Maier & Neustadt, P.C.

(57) ABSTRACT

The invention provides compounds with antagonism against excitatory amino acid receptors, in particular, AMPA receptor having 6-substituted heteroquinolinecarboxylic acid derivatives and addition salts thereof as effective ingredients, and processes for the preparation of both. These compounds relate to 6-substituted heteroquinolinecarboxylic acid derivatives represented by a general formula (1)

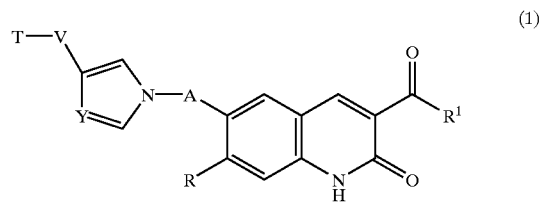

(1)

(wherein A denotes a single bond or methylene ($CH_2$), Y denotes a nitrogen atom or =CH—, V denotes a single bond or methylene ($CH_2$), T denotes a hydroxyl group, amino group, lower alkoxycarbonyl group, carboxyl group, aldehyde group or the like, R denotes a nitro group, trifluoromethyl group or halogen atom, and $R^1$ denotes a hydroxyl group or lower alkoxy group), and addition salts thereof.

20 Claims, No Drawings

6-SUBSTITUTED HETEROQUINOLINECARBOXYLIC ACID DERIVATIVES AND ADDITION SALTS THEREOF AND PROCESSES FOR THE PREPARATION OF BOTH

This application is a 371 of PCT/JP00/01077, filed Feb. 25, 2000.

TECHNICAL FIELD

The present invention relates to 6-substituted heteroquinolinecarboxylic acid derivatives and their addition salts effective for the therapy of disorder of cerebral nerve cells as antagonists against excitatory amino acid receptors, in particular, as selective antagonists against AMPA receptor in non-NMDA receptor, processes for the preparation of both, and a medicinal composition containing these compounds.

BACKGROUND TECHNOLOGIES

The glutamic acid being excitatory amino acid is a main excitatory transmitter substance in the central nervous system of vertebrates, and is known as an amino acid contained most rich in brain. It is known, however, that, when releasing from nervous axon terminals exceeding the physiological threshold, it excessively excites the glutamic acid receptor of post-synapse to cause the death of nerve cells. This is called excitotoxicity.

In recent years, it has been clarified that the death of nerve cells due to glutamic acid concerns deeply in various diseases of cerebral nerve such as cerebral hemorrhage, head trauma, epilepsy, Huntington's disease, Parkinson's disease, amyotrophic lateral sclerosis and Alzheimer's disease. It is considered therefore that, if such excitotoxicity could be prevented effectively, a potential to the therapy for these intractable diseases, for which there are virtually no therapeutic means at present, would be opened.

Roughly classifying, the glutamic acid receptor is divided into ion channel type receptor and G protein-binding type receptor, and this ion channel type receptor is further divided into NMDA (N-methyl-D-aspartic acid) receptor and non-NMDA receptor. Moreover, the latter non-NMDA receptor is classified into AMPA (α-amino-3-hydroxy-5-methyl-4-isooxazol-propionic acid) receptor and KA (kainic acid) receptor.

Studies on these excitatory amino acid receptors are being put forward, and, above all, with the drug with antagonism against AMPA receptor in non-NMDA receptor, it is known that the adverse effects (learning and memory disturbances, schizophrenia-like symptom, etc.), which the drugs (MK-801 etc.) with antagonism against NMDA receptor have, are not expressed (Neurosci. Biobehav. Rev., 1992, 16, 13–24; J. Pharmacol. Exp. Ther., 1958, 245, 969–974), and that the protective effect on cerebral nerve can be expected even by the administration after ischemia (Science, 1990, 247, 571–574).

Moreover, with the compounds with quinoxalinedione structure and with antagonism against AMPA receptor such as NBQX, drawbacks of causing kidney disturbance that is considered based on physicochemical properties, and the like are reported (J. Cereb. Blood Flow Metab., 1994, 14, 251–261), hence they cannot be said to be satisfactory compounds.

Now, as the compounds with similar structure to quinolinecarboxylic acid derivatives, compounds represented by a general formula (13)

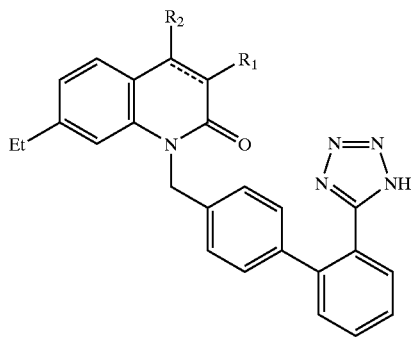

(13)

(wherein $R_1$ denotes aldehyde group, amide group, carboxyl group, etc. and $R_2$ denotes hydrogen atom), described in Korean J. Med. Chem., 5 (1), 28–37 (1995) by Dong-A Pharmaceutical Research Laboratories as compounds with antagonism against angiotensin II, compounds represented by a general formula (14)

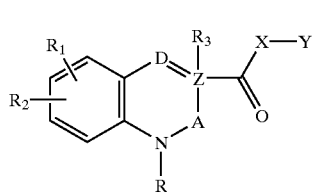

(14)

(wherein R denotes hydrogen atom or alkyl group, $R_1$ and $R_2$ denote hydrogen atoms, halogens, alkyl groups, alkoxycarbonyl groups, nitro groups, cyano groups, etc., $R_3$ denotes hydrogen atom, alkyl group, aryl group or aralkyl group, or $R_3$ is absent, A denotes CO, CS, etc., Z denotes nitrogen atom when $R_3$ is absent and D—Z is single bond, or Z is carbon atom, D denotes C—R when D—Z is double bond, X denotes oxygen atom, N—R, etc., and Y denotes substituted aminoalkyl group, quinuclidyl group, etc.), described in EP 382687 by Instituto De Angeli S.p.A, as compounds with antimuscarine function, and compounds represented by a general formula (15)

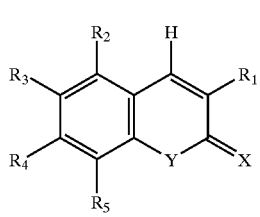

(15)

(wherein $R_1$ denotes cyano group, carboxyl group, alkoxycarbonyl group, amide group, nitro group, acetylamino group, etc., X denotes oxygen atom etc., Y denotes oxygen atom, sulfur atom or NH, $R_2$ and $R_4$ denote hydrogen atoms, hydroxyl groups, amino groups, trifluoromethyl groups, alkyl groups, etc., $R_3$ denotes hydroxyl group, amino group, alkylamino group, nitroso group, trifluoromethyl group, etc., and $R_5$ denotes hydroxyl group, alkyl group, halogen atom, etc.), described in WO93/16064 by Biosignal Co. as compounds with anticancer function (tyrosinekinase inhibitory function), are known. However, none of these compounds as described above have asymmetric substituents at 6- and 7-positions, and it is also not described that they have the antagonism against AMPA receptor in excitatory amino acid receptors.

Moreover, compounds represented by a general formula (16)

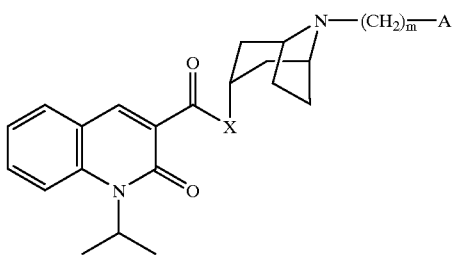

(16)

(wherein X denotes oxygen atom or NH, m denotes 0 to 6, and A denotes haloalkyl group, hydroxyl group, alkoxy group, carboxyl group, cyano group, amide group, etc.), described in WO95/31455 by Taisho Pharmaceutical Co. as compounds with antagonism against serotonin 4 receptor, and compounds represented by a general formula (17)

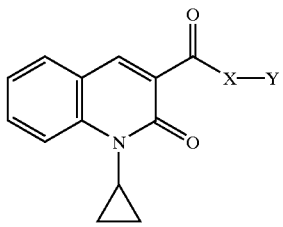

(17)

(wherein X denotes O or NH, and Y denotes 2-(diethylamino)ethyl, 8-methyl-8-azabicyclo-[3,2,1]octa-3-yl, quinuclidine-3-yl, 1-ethylpiperidine-4-yl, etc.), described in Jpn. Kokai Tokkyo Koho JP 08,311,033 by the same company as compounds with antagonism against serotonin 4 receptor, are known. In these compounds, however, no substituents exist on benzene ring, the structure is different from that of the inventive compounds, and it is not described that they have the antagonism against AMPA receptor in excitatory amino acid receptors.

Moreover, compounds represented by a general formula (18)

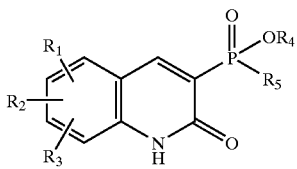

(18)

(wherein $R_1$, $R_2$ and $R_3$ denote hydrogen atoms, halogen atoms, alkyl groups, nitro groups, cyano groups, aminosulfonyl groups, etc., and $R_4$ and $R_5$ denote hydrogen atoms, alkyl groups, etc.), are opened to public in EP 640612 by Adeal et compagnie as compounds with inhibitory action on the pathologic symptoms relevant to hyperactivity through the route of excitatory amino acid, and, as synthetic intermediates of this general formula (18), compounds represented by a general formula (19)

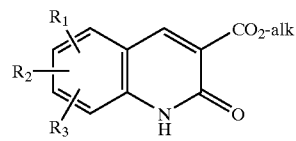

(19)

(wherein $R_1$, $R_2$ and $R_3$ are as described above), and compounds represented by a general formula (20)

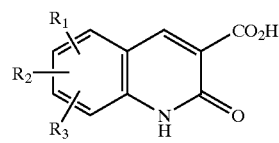

(20)

(wherein $R_1$, $R_2$ and $R_3$ are as described above), are transcribed. However, the fact that these synthetic intermediates have the antagonism against AMPA receptor in excitatory amino acid receptors is not described, and, in these compounds, those with substituents at 6- and 7-positions as the inventive compounds are of symmetric type, hence the structure is different from that of the inventive compounds.

Moreover, compounds represented by a general formula (21)

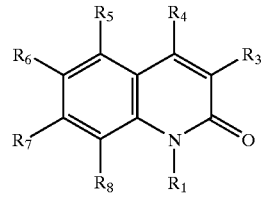

(21)

(wherein $R_1$ and $R_8$ denote hydrogen atoms or alkyl groups, $R_3$ denotes hydrogen atom, alkyl group, carboxyl group, cyano group, etc., $R_4$ denotes hydrogen atom, alkyl group, alkoxy group, etc., $R_5$ denotes hydrogen atom, amino group, etc., $R_6$ denotes hydrogen atom, and $R_7$ denotes hydroxyl group, amino group, alkylamino group, etc.), described in Jpn. Kokai Tokkyo Koho JP 03,162,483 by Pioneer Electronics Co. as compounds for fluorescent material in organic luminescence device, are known. These compounds however are irrelevant to medicinal drugs, and it is not described that they have the antagonism against AMPA receptor in excitatory amino acid receptors as well.

Moreover, recently, compounds represented by a general formula (22)

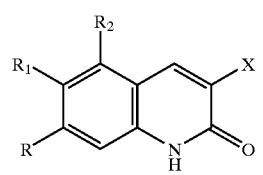

(22)

(wherein R, $R_1$ and $R_2$ denote hydrogen atoms, chlorine atoms, fluorine atoms or nitro groups, and X denotes carboxylic acid, phosphoric acid, boric acid, amide, etc.), are reported in J. Med. Chem., 39, 197–206 (1996) by Alex A. Cordi et al, with respect to the conversion of functional group at 3-position of 2-oxoquinoline skeleton as antagonists against excitatory amino acid. Among these compounds, however, they aimed to compounds, X being phosphoric acid in the general formula (22), and, in addition, those with asymmetric substituents at 6- and 7-position of quinoline ring as the inventive compounds are not reported. Also, the antagonism against AMPA and the antagonism against glycine reported are not considered to be sufficient.

Moreover, quinolone derivatives are described in WO 93/10783 by Merck Sharp and Dohme Co. as compounds with antagonism against NMDA and AMPA receptors. However, the disclosure of compounds cannot be said to be sufficient, and, in addition, the structure is different from that of the inventive compounds with characteristic substituents at 6-position of quinoline ring.

Moreover, the disclosed pharmacological data are also only for NMDA receptor and no concrete data are disclosed against AMPA receptor, as the inventive compounds.

The invention is to provide compounds with antagonism against receptor of glutamic acid that is considered to be an etiology bringing about the memory disorder or dementia due to said diseases and selective death of cells, in particular, with high affinity and selectivity against AMPA receptor in non-NMDA receptor and protective effect on cerebral nerve cells.

DISCLOSURE OF THE INVENTION

As a result of diligent studies exploring an antagonist against excitatory amino acid receptors effective for the therapy of disorder of cerebral nerve cells, in particular, a selective antagonist against AMPA receptor in non-NMDA receptor, aiming at the development of novel therapeutic agent for the disorder of cerebral nerve cells, the inventors have found that the inventive 6-substituted heteroquinolinecarboxylic acid derivatives and addition salts thereof have excellent antagonism against AMPA receptor.

Namely, according to the invention, it has been found that 6-substituted heteroquinolinecarboxylic acid derivatives represented by a general formula (1)

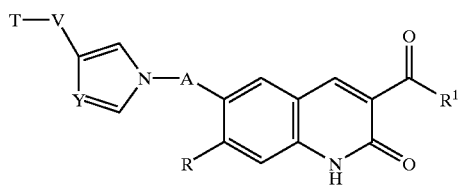

(1)

(wherein A denotes a single bond or methylene (CH$_2$),
Y denotes a nitrogen atom or =CH—,
V denotes a single bond or methylene (CH$_2$),
T denotes a hydroxyl group, amino group, lower alkoxycarbonyl group, carboxyl group, aldehyde group, general formula (2)

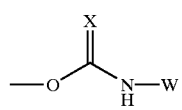

(2)

(wherein X denotes an oxygen atom or sulfur atom, and W denotes an aralkyl group, phenyl group, naphthyl group, 5- or 6-membered heterocycle and its condensed ring (these may have one or more substituents on aromatic ring or heterocycle), lower alkyl group which may be substituted with halogen, or cycloalkyl group), or general formula (3)

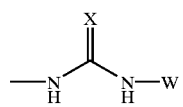

(3)

(wherein X denotes an oxygen atom or sulfur atom, and W denotes an aralkyl group, phenyl group, naphthyl group, 5- or 6-membered heterocycle and its condensed ring (these may have one or more substituents on aromatic ring or heterocycle), lower alkyl group which may be substituted with halogen, or cycloalkyl group),
R denotes a nitro group, trifluoromethyl group or halogen atom, and
R$^1$ denotes a hydroxyl group or lower alkoxy group), and addition salts thereof have excellent antagonism against AMPA receptor, leading to the completion of the invention.

In the general formula (1) of the inventive compounds, preferably, compounds, R being nitro group, trifluoromethyl group or chloro group, R$^1$ being hydroxyl group or lower alkoxy group, and A being single bond, are mentioned. More preferably, compounds, R being nitro group, trifluoromethyl group or chloro group, R$^1$ being hydroxyl group, V being methylene (CH$_2$), and X being oxygen atom in the general formula (2) or general formula (3) for T, are mentioned. As these preferable compounds, compounds shown below, namely, 1,2-dihydro-7-nitro-2-oxo-6-(4-((phenylcarbamoyloxy)methyl)imidazole-1-yl)quinoline-3-carboxylic acid, 6-(4-(((2-bromophenyl)carbamoyloxy)methyl)imidazole-1-yl)-1,2-dihydro-7-nitro-2-oxoquinoline-3-carboxylic acid, 6-(4-(((3-bromophenyl)carbamoyloxy)methyl)imidazole-1-yl)-1,2-dihydro-7-nitro-2-oxoquinoline-3-carboxylic acid, 6-(4-(((4-bromophenyl)carbamoyloxy)methyl)imidazole-1-yl)-1,2-dihydro-7-nitro-2-oxoquinoline-3-carboxylic acid, 6-(4-(((2-fluorophenyl)carbamoyloxy)methyl)imidazole-1-yl)-1,2-dihydro-7-nitro-2-oxoquinoline-3-carboxylic acid, 6-(4-(((4-fluorophenyl)carbamoyloxy)methyl)imidazole-1-yl)-1,2-dihydro-7-nitro-2-oxoquinoline-3-carboxylic acid, 1,2-dihydro-6-(4-(((2,4-difluorophenyl)carbamoyloxy)methyl)imidazole-1-yl)-7-nitro-2-oxoquinoline-3-carboxylic acid, 1,2-dihydro-6-(4-(((2,5-difluorophenyl)carbamoyloxy)methyl)imidazole-1-yl)-7-nitro-2-oxoquinoline-3-carboxylic acid, 1,2-dihydro-6-(4-(((4-methoxyphenyl)carbamoyloxy)methyl)imidazole-1-yl)-7-nitro-2-oxoquinoline-3-carboxylic acid, 1,2-dihydro-6-(4-(((4-methylphenyl)carbamoyloxy)methyl)imidazole-1-yl)-7-nitro-2-oxoquinoline-3-carboxylic acid, 1,2-dihydro-7-nitro-2-oxo-6-(4-(((4-trifluoromethylphenyl)carbamoyloxy)methyl)imidazole-1-yl)quinoline-3-carboxylic acid, 6-(4-(((4-ethoxycarbonylphenyl)carbamoyloxy)methyl)imidazole-1-yl)-1,2-dihydro-7-nitro-2-oxoquinoline-3-carboxylic acid, 6-(4-(((3-ethoxycarbonylphenyl)carbamoyloxy)methyl)imidazole-1-yl)-1,2-dihydro-7-nitro-2-oxoquinoline-3-carboxylic acid, 1,2-dihydro-7-nitro-2-oxo-6-(4-((N-phenylmethylcarbamoyloxy)methyl)imidazole-1-yl)quinoline-3-carboxylic acid, 6-(4-(((3-carboxyphenyl)carbamoyloxy)methyl)imidazole-1-yl)-1,2-dihydro-7-nitro-2-oxoquinoline-3-carboxylic acid, 6-(4-(((4-carboxyphenyl)carbamoyloxy)methyl)imidazole-1-yl)-1,2-dihydro-7-nitro-2-oxoquinoline-3-carboxylic acid, 6-(4-(((4-carboxy-2-fluorophenyl)carbamoyloxy)methyl)imidazole-1-yl)-1,2-dihydro-7-nitro-2-oxoquinoline-3-carboxylic acid, 6-((((2- fluorophenyl)aminocarbonylamino)methyl)imidazole-1-yl)-1,2-dihydro-7-nitro-2-oxoquinoline-3-carboxylic acid, 6-((((4-carboxy-2-fluorophenyl)aminocarbonylamino)methyl)imidazole-1-yl)-1,2-dihydro-7-nitro-2-oxoquinoline-3-carboxylic acid, 6-((((3-carboxyphenyl)aminocarbonylamino)methyl)imidazole-1-yl)-1,2-dihydro-7-nitro-2-oxoquinoline-3-carboxylic acid, 6-((((4-carboxyphenyl)aminocarbonylamino)methyl)imidazole-1-yl)-1,2-dihydro-7-nitro-2-oxoquinoline-3-carboxylic acid, 6-(4-(((4-carboxyphenyl)carbamoyloxy)methyl)imidazole-1-yl)-1,2-dihydro-2-oxo-7-trifluoromethylquinoline-3-carboxylic acid, 6-(4-(((4-carboxymethylphenyl)carbamoyloxy)methyl)imidazole-1-yl)-1,2-dihydro-7-trifluoromethyl-2-oxoquinoline-3-carboxylic acid, 6-(4-(((4-carboxy-2-fluorophenyl)carbamoyloxy)methyl)imidazole-1-yl)-1,2-dihydro-7-trifluoromethyl-2-oxoquinoline-3-carboxylic acid, 6-((((4-carboxyphenyl)aminocarbonylamino)methyl)imidazole-1-yl)-1,2-dihydro-7-trifluoromethyl-2-oxoquinoline-3-carboxylic acid, 6-((((4-carboxymethylphenyl)aminocarbonylamino)methyl)imidazole-1-yl)-1,2-dihydro-7-trifluoromethyl-2-oxoquinoline-3-carboxylic acid, 6-((((4-carboxyphenyl)aminocarbonylamino)methyl)pyrrole-1-yl)-1,2-dihydro-7-trifluoromethyl-2-oxoquinoline-3-carboxylic acid, 6-((((4-carboxymethylphenyl)aminocarbonylamino)methyl)pyrrole-1-yl)-1,2-dihydro-7-trifluoromethyl-2-oxoquinoline-3-carboxylic acid, 6-(4-(((4-carboxyphenyl)carbamoyloxy)methyl)imidazole-1-yl)-7-chloro-1,2-dihydro-2-oxoquinoline-3-carboxylic acid, 6-(4-(((4-carboxymethyl-phenyl)carbamoyloxy)methyl)imidazole-1-yl)-7-chloro-1,2-dihydro-2-oxoquinoline-3-carboxylic acid, 6-((((4-carboxyphenyl)aminocarbonylamino)methyl)imidazole-1-yl)-7-chloro-1,2-dihydro-2-oxoquinoline-3-carboxylic acid, 6-((((4-carboxymethylphenyl)aminocarbonylamino)methyl)imidazole-1-yl)-7-chloro-1,2-dihydro-2-oxoquinoline-3-carboxylic acid, 6-((((4-carboxyphenyl)aminocarbonylamino)methyl)pyrrole-1-yl)-7-chloro-1,2-dihydro-2-oxoquinoline-3-carboxylic acid, 6-((((4-carboxymethylphenyl)aminocarbonylamino)methyl)pyrrole-1-yl)-7-chloro-1,2-dihydro-2-oxoquinoline-3-carboxylic acid, and the like can be mentioned.

Best Embodiment to Put the Invention into Practice

In the description of the general formula (1) of the invention, for "substituents" in the phrase of "aralkyl group, phenyl group, naphthyl group, 5- or 6-membered heterocycle and its condensed ring (these may have one or more substituents on aromatic ring or heterocycle)", halogen atom, hydroxyl group, lower alkyl group which may be substituted with halogen atom, lower alkoxy group, lower alkylthio group, lower alkoxycarbonyl group, nitro group, amino group which may be substituted, cyano group, carboxyl group, aldehyde group, carboxy lower alkyl group, etc. are mentioned, for "lower alkyl groups", straight chain or branched ones with carbon atoms of 1 to 6 such as methyl, ethyl, n-propyl and iso-propyl are mentioned, for "cycloalkyl groups", ones with carbon atoms of 3 to 7 such as cyclopropyl, cyclopentyl and cyclohexyl are mentioned, for "halogen atoms", fluorine, chlorine, bromine and iodine are mentioned, for "lower alkoxy groups", straight chain or branched ones with carbon atoms of 1 to 4 such as methoxy, ethoxy and propoxy are mentioned, for "lower alkylthio groups", straight chain or branched ones with carbon atoms of 1 to 6 such as methylthio, ethylthio and propylthio are mentioned, for "lower alkoxycarbonyl groups", straight chain or branched ones with carbon atoms of 1 to 4 such as methoxycarbonyl and ethoxycarbonyl are mentioned, for "aralkyloxy groups", benzyloxy, phenylethyloxy and phenylpropyloxy are mentioned, for "aralkylthio groups", benzylthio, phenylethylthio and phenylpropylthio are mentioned, and, for "amino groups which may be substituted", amino groups may be substituted with acyl group or arylsulfonyl group, for example, acetyl, methanesulfonyl, phenylsulfonyl, etc., or they may be substituted with lower alkyl group which may be substituted with 1 to 2 halogen atoms, phenyl group which may have 1 to 2 substituents or aralkyl group which may have 1 to 2 substituents. The substituents referred to so here are "substituents" as explained above.

Furthermore, in the description, "heterocycles" in the phrase of "aralkyl group, phenyl group, naphthyl group, 5- or 6-membered heterocycle and its condensed ring (these may have one or more substituents on aromatic ring or heterocycle)" are saturated or unsaturated monocyclic or polycyclic heterocycle groups which may have one or more substituents and which can contain one or more nitrogen, oxygen or sulfur atoms, and, for example, pyrrolidyl, piperidyl, piperazyl, morpholyl, thiomorpholyl, furanyl, thienyl, pyrazolyl, imidazolyl, oxazolyl, thiazolyl, pyridyl, pyrimidyl, pyridazyl, pyrazyl, etc. are mentioned. "Its condensed ring" represents benzene-condensed rings of said "heterocycles" and, for example, indolyl, tetrahydroquinolyl, benzoxazolidinyl, benzothiazolidinyl, benzofuranyl, benzothienyl, benzimidazolyl, quinolyl, isoquinolyl, quinazolyl, quinoxalyl, cinnolyl, etc. are mentioned.

The compounds of the invention are prepared, for example, through preparative processes shown below.

Compounds represented by the general formula (1) can be synthesized by reacting compounds represented by a general formula (4)

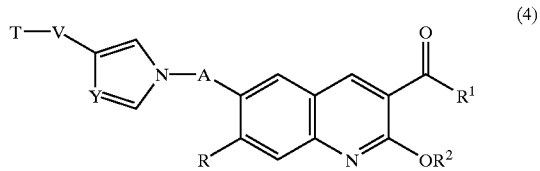

(4)

(wherein A, Y, V, T, R and $R^1$ are as described above, and $R^2$ denotes a lower alkyl group which may be substituted with halogen atom or aralkyl group which may have one or more substituents), for 0.5 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid, mixed acid thereof or the like.

Moreover, compounds represented by the general formula (1) can also be synthesized, in the case of $R^1$ being lower alkoxy group among compounds represented by the general formula (4)

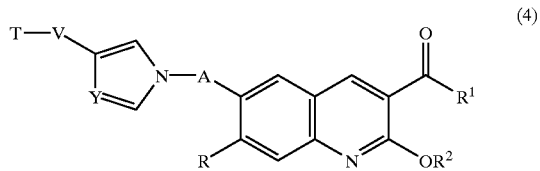

(4)

(wherein A, Y, V, T, R, $R^1$ and $R^2$ are as described above), by reacting those compounds for 0.5 to 72 hours at 20 to 100° C. in a suitable solvent, for example, water, methanol, ethanol or the like, using a suitable alkali, for example, potassium hydroxide, sodium hydroxide, lithium hydroxide or the like to convert to carboxylic acid, and then reacting for 0.5 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid, mixed acid thereof or the like.

Moreover, compounds represented by the general formula (1) can also be synthesized, in the case of $R^1$ being lower alkoxy group among compounds represented by the general formula (4)

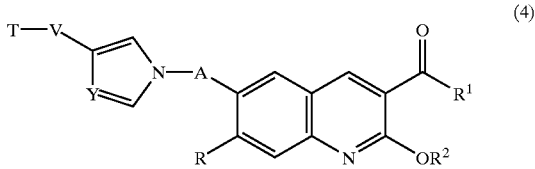

(4)

(wherein A, Y, V, T, R, $R^1$ and $R^2$ are as described above), by reacting those compounds for 3 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid, mixed acid thereof or the like to deprotect $R^2$, and then reacting for 0.5 to 72 hours at 20 to 100° C. in a solvent of water, methanol, ethanol or the like, using a suitable alkali, for example, potassium hydroxide, sodium hydroxide, lithium hydroxide or the like.

Moreover, compounds, $R^1$ being lower alkoxy group among compounds represented by the general formula (1), those compounds are reacted for 0.5 to 10 hours at 20 to 100° C. in a suitable solvent of water, methanol, ethanol or the like, using a suitable alkali, for example, potassium hydroxide, sodium hydroxide, lithium hydroxide or the like to synthesize compounds, $R^1$ being hydroxyl group.

Moreover, compounds, Y being =CH— among compounds represented by the general formula (1) can also be synthesized by reacting compounds represented by a general formula (5)

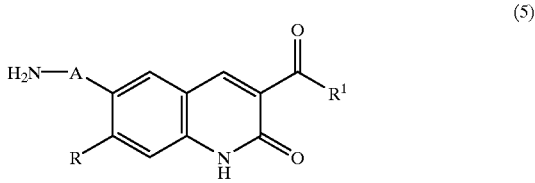

(5)

(wherein A, R and $R^1$ are as described above), with compounds represented by a general formula (6)

(6)

(wherein T and V are as described above, and $R^3$ denotes a lower alkyl group which may be substituted with halogen or aralkyl group which may have one or more substituents), for 0.5 to 5 hours at 20 to 120° C. without solvent or in a suitable solvent, for example, tetrahydrofuran, benzene, toluene, acetic acid, ethanol, methanol or the like (suitable inorganic or organic acid, for example, hydrochloric acid, sulfuric acid, p-toluenesulfonic acid or the like may be added).

Moreover, compounds, T being represented by the general formula (2) or general formula (3) among compounds represented by the general formula (1), can also be synthesized by reacting compounds represented by a general formula (7)

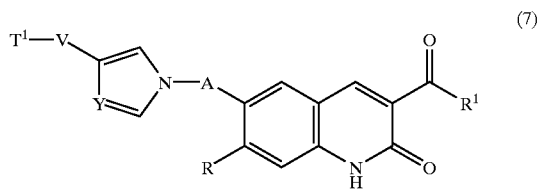

(7)

(wherein A, Y, V, R and $R^1$ are as described above, and $T^1$ denotes a hydroxyl group or amino group), with compounds represented by a general formula (8)

$$Z-N=C=Xa \qquad (8)$$

(wherein Z denotes an aralkyl group, phenyl group, naphthyl group, 5- or 6-membered heterocycle or its condensed ring (these may have one or more substituents on aromatic ring or heterocycle), lower alkyl group which may be substituted with halogen, or cycloalkyl group, and Xa denotes an oxygen or sulfur atom), for 1 to 15 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable organic base, for example, triethylamine, pyridine or the like.

Moreover, they can also be synthesized by converting compounds represented by a general formula (9)

$$Z-A_1-D \qquad (9)$$

(wherein Z is as described above, $A_1$ denotes single bond, and D denotes an amino group, carboxyl group, amide group or lower alkoxycarbonyl group), to isocyanic (isothiocyanic) esters or carbamic chlorides through already known process, in place of the general formula (8), and then reacting with general formula (7) similarly to general formula (8).

For example, in the case of D being amino group, they can be converted to carbamic chlorides or isocyanic (isothiocyanic) esters by reacting with phosgene (thiophosgene), phosgene dimer (2,2,2-trichloromethyl chloroformate) or its homologue (4-nitrophenyl chloroformate etc.) for 1 to 5 hours at −10 to 50° C. in a suitable solvent, for example, tetrahydrofuran, dioxane, benzene, toluene or the like, without base or using a suitable organic base, for example, triethylamine or the like. Further, they can be converted to isocyanic (isothiocyanic) esters by using Crutius rearrangement reaction or Schmidt rearrangement reaction after converted carboxyl group to acid azide in the case of D being carboxyl group, and by using Hofmann rearrangement reaction in the case of D being amide group. Moreover, in the case of D being carboxyl group, it is also possible to convert to isocyanic (isothiocyanic) esters in one pot using DPPA (diphenylphosphoryl azide).

Moreover, compounds represented by the general formula (1) can also be synthesized by reacting compounds represented by a general formula (23)

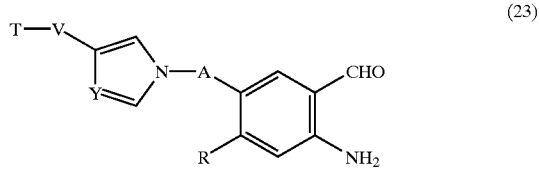

(23)

(wherein A, Y, V, T and R are as described above), with malonic diesters represented by a general formula (24)

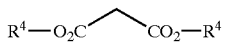
(24)

(wherein $R^4$ denotes a lower alkyl group), for 2 to 24 hours at 25 to 100° C. in a suitable solvent, for example, ethanol, methanol, tetrahydrofuran or the like, in the presence of a suitable base, for example, sodium ethoxide, sodium methoxide, potassium ter-butoxide, potassium hydroxide or the like.

Moreover, compounds represented by the general formula (1) can be synthesized by reacting compounds represented by a general formula (25)

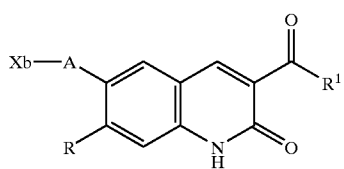
(25)

(wherein A, R and $R^1$ are as described above, and Xb denotes a halogen atom), with compounds represented by a general formula (12)

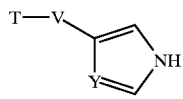
(12)

(wherein Y, V and T are as described above), for 0.5 to 24 hours at 20 to 160° C. without solvent or in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds, T being represented by the general formula (2) or general formula (3) among compounds represented by the general formula (4), can also be synthesized by reacting compounds represented by a general formula (10)

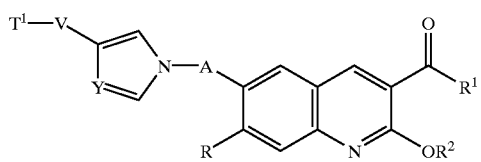
(10)

(wherein A, Y, V, R, $R^1$, $R^2$ and $T^1$ are as described above), with compounds represented by the general formula (8)

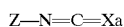
(8)

(wherein Z and Xa are as described above), for 1 to 15 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable organic base, for example, triethylamine, pyridine or the like.

Moreover, they can also be synthesized by converting compounds represented by a general formula (9)

(9)

(wherein Z, $A_1$ and D are as described above), to isocyanic (isothiocyanic) esters or carbamic chlorides through already known process, in place of the general formula (8), and then reacting with general formula (7) similarly to general formula (8).

For example, in the case of D being amino group, they can be converted to carbamic chlorides or isocyanic (isothiocyanic) esters by reacting with phosgene (thiophosgene), phosgene dimer (2,2,2-trichloromethyl chloroformate) or its homologue (4-nitrophenyl chloroformate etc.) for 1 to 5 hours at −10 to 50° C. in a suitable solvent, for example, tetrahydrofuran, dioxane, benzene, toluene or the like, without base or using a suitable organic base, for example, triethylamine or the like.

Further, they can be converted to isocyanic (isothiocyanic) esters by using Crutius rearrangement reaction or Schmidt rearrangement reaction after converted carboxyl group to acid azide in the case of D being carboxyl group, and by using Hofmann rearrangement reaction in the case of D being amide group. Moreover, in the case of D being carboxyl group, it is also possible to convert to isocyanic (isothiocyanic) esters in one pot using DPPA (diphenylphosphoryl azide).

Moreover, compounds represented by the general formula (4) can be synthesized by reacting compounds represented by a general formula (11)

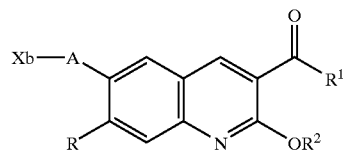
(11)

(wherein A, Xb, R, $R^1$ and $R^2$ are as described above), with compounds represented by a general formula (12)

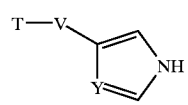
(12)

(wherein Y, T and V are as described above), for 0.5 to 24 hours at 20 to 160° C. without solvent or in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Here, compounds, A being single bond among compounds represented by the general formula (11), can be synthesized by reacting compounds represented by a general formula (25)

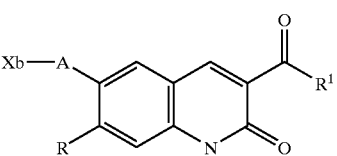
(25)

(wherein A, Xb, R and $R^1$ are as described above), with alkyl halide, for example, methyl iodide or the like, or aralkyl halide, for example, 4-methoxybenzyl chloride or the like, for 2 to 10 hours at 20 to 120° C. in a suitable solvent, for example, benzene, toluene, chloroform, methylene chloride, tetrahydrofuran or the like, using a suitable silver catalyst, for example, silver oxide, silver carbonate or the like.

Moreover, they can also be synthesized by reacting compounds represented by the general formula (25) for 2 to 6 hours at 0 to 120° C. in a suitable solvent, for example, benzene, toluene, chloroform, methylene chloride, tetrahydrofuran or the like, using borate, for example, tetramethyloxonium borate or the like.

Moreover, compounds, A being methylene (CH$_2$) among compounds represented by the general formula (11) can be synthesized by reacting compounds represented by a general formula (26)

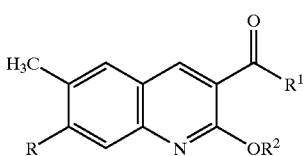

(26)

(wherein R, R$^1$ and R$^2$ are as described above), for 1 to 12 hours at 20 to 100° C. in a suitable solvent, for example, carbon tetrachloride, chloroform, acetic acid or the like, using a halogenating agent, for example, N-bromosuccinimide (NBS), N-chlorosuccinimide (NCS), bromine or the like.

Moreover, compounds represented by the general formula (5) can be synthesized by reacting compounds represented by a general formula (27)

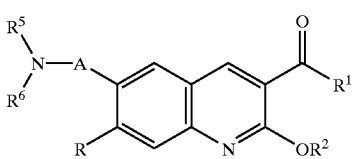

(27)

(wherein A, R, R$^1$ and R$^2$ are as described above, and R$^5$ and R$^6$ identically or differently denote hydrogen atoms or protective groups of amino group), for 3 to 72 hours at 20 to 120° C. in a suitable solvent, for example, water, acetic acid, methanol, ethanol or the like, using a suitable acid, for example, hydrochloric acid, sulfuric acid, hydrobromic acid, trifluoroacetic acid, mixed acid thereof or the like.

Here, compounds represented by the general formula (27) can be synthesized by reacting compounds represented by the general formula (11)

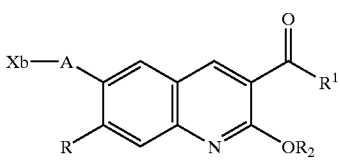

(11)

(wherein A, R, R$^1$, R$^2$ and Xb are as described above), with general formula (28)

R$^5$R$^6$—NH  (28)

(wherein R$^5$ and R$^6$ are as described above), for 0.5 to 48 hours at 20 to 160° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds (31), A being single bond and R being trifluoromethyl group among compounds represented by the general formula (5), can be synthesized through publicly known processes shown in Scheme 1.

Scheme 1

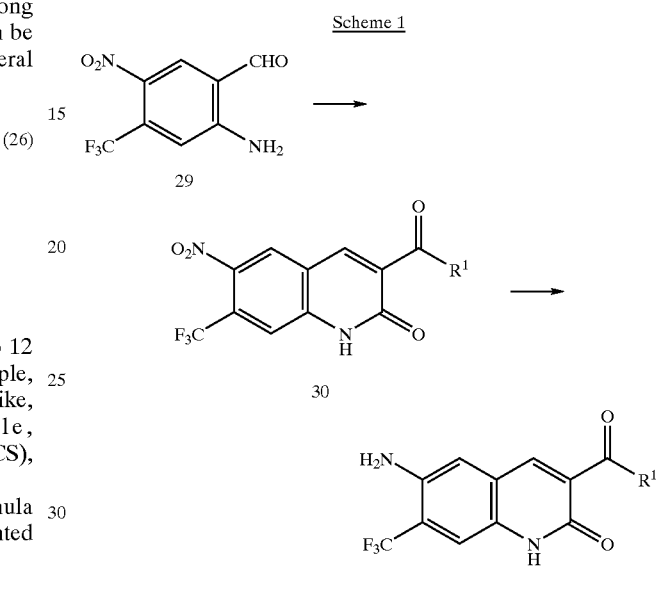

(wherein R$^1$ is as described above)

Namely, compounds (29) are reacted with malonic esters, for example, diethyl malonate or the like, for 2 to 24 hours at 25 to 100° C. in a suitable solvent, for example, alcohol such as ethanol or methanol, tetrahydrofuran, N,N-dimethylformamide or the like, in the presence of a suitable base, for example, sodium ethoxide, potassium ter-butoxide, potassium hydroxide or the like, to convert to compounds (30), and then these are subject to reduction through catalytic hydrogenation, that is, hydrogenated for 2 to 24 hours at 25 to 80° C. and at ambient pressure to 5 atm (507 KPa) in a suitable solvent, for example, ethanol, methanol, acetic acid or the like in the presence of a suitable catalyst, for example, palladium on carbon, platinum oxide, rhodium on alumina or the like, thus allowing to synthesize compounds (31). Also, they can be synthesized by reacting compounds (30) for 1 to 7 hours at 25 to 100° C. in a suitable solvent, for example, ethanol, dilute hydrochloric acid, acetic acid or mixed solvent thereof in the presence of tin chloride, zinc, iron, sodium hydrosulfite or the like.

Here, compound represented by the general formula (29) can be synthesized as shown in following Scheme 2.

Scheme 2

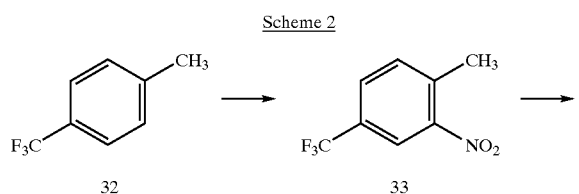

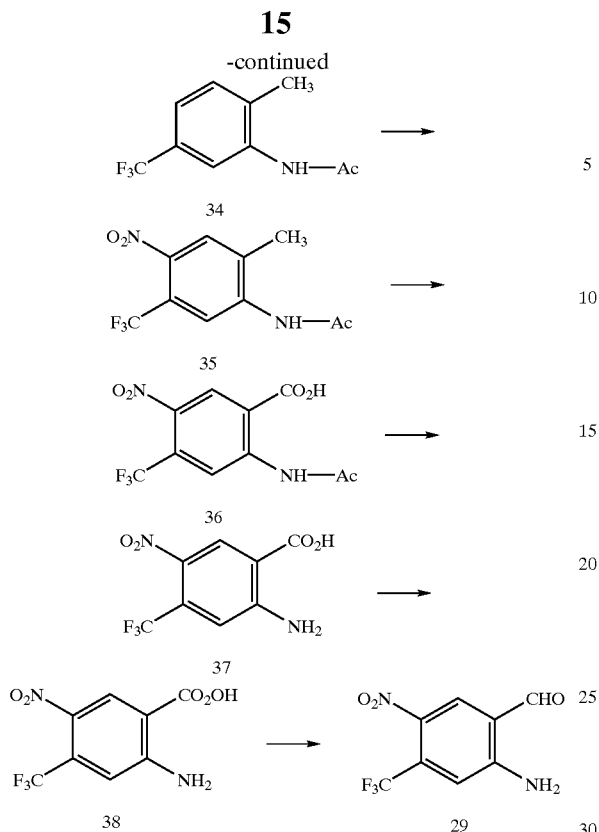

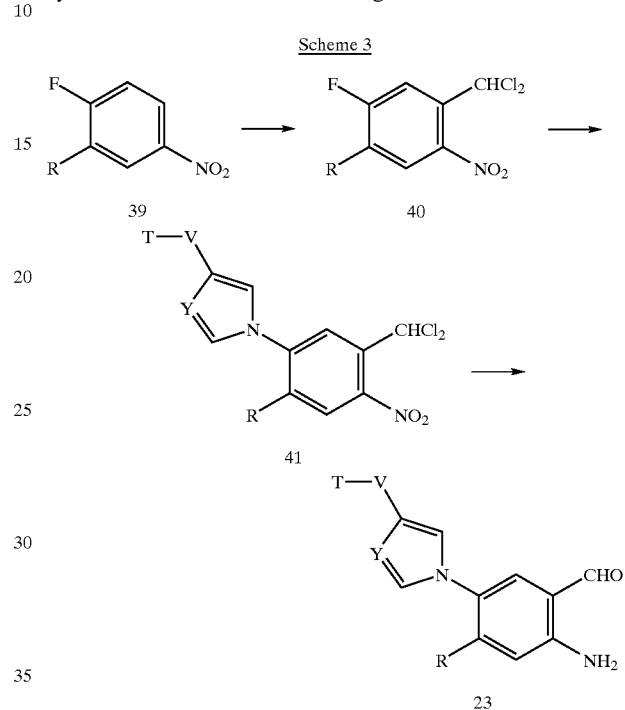

Namely, available or synthesizable compound (32) is reacted for 0.5 to 2 hours at −10 to 80° C. in a suitable solvent, for example, nitromethane, acetic acid, sulfuric acid or the like, using a suitable nitrating agent, for example, concentrated nitric acid, fuming nitric acid, potassium nitrate, acetyl nitrate or the like to convert to compound (33), and this is subject to reduction through catalytic hydrogenation, that is, hydrogenated for 2 to 24 hours at 25 to 80° C. and at atmospheric pressure to 5 atm (507 KPa) in a suitable solvent, for example, ethanol, methanol, acetic acid or the like in the presence of a suitable catalyst, for example, palladium on carbon, platinum oxide, rhodium-alumina or the like, followed further by aceylation, to convert to compound (34). This is reacted for 0.5 to 2 hours at −10 to 80° C. in a suitable solvent, for example, nitromethane, acetic acid, sulfuric acid or the like, using a suitable nitrating agent, for example, concentrated nitric acid, fuming nitric acid, potassium nitrate, acetyl nitrate or the like to convert to compound (35), then this is reacted for 1 to 15 hours at 0 to 120° C. in a suitable solvent, for example, water, acetone or the like, using a suitable oxidizing agent, for example, potassium permanganate, sodium periodate or the like to convert to compound (36), and successively this is hydrolyzed for 1 to 10 hours at 20 to 100° C. in a suitable solvent, for example, water, ethanol, methanol or the like or mixed solution thereof, using a suitable base, for example, sodium hydroxide, potassium hydroxide or the like, or it is hydrolyzed for 1 to 10 hours at 20 to 100° C. in a suitable solvent, for example, water, ethanol, methanol or the like or mixed solution thereof, using a suitable acid, for example, hydrochloric acid, hydrobromic acid or the like, thereby converting to compound (37). Next, compound (37) is reacted for 1 to 10 hours at 20 to 150° C. in a suitable solvent, for example, ether, tetrahydrofuran, dioxane or the like, using a suitable reducing agent, for example, borane complex such as borane-tetrahydrofuran complex, borane-dimethyl sulfide complex, borane-pyridine complex or the like to convert to compound (38), and further this is reacted for 1 to 24 hours at 20 to 100° C. in a suitable solvent, for example, chloroform, methylene chloride, tetrahydrofuran or the like, using a suitable oxidizing agent, for example, manganese dioxide or the like, thus allowing to convert to compound (29).

Moreover, compounds, A being single bond among compounds represented by the general formula (23), can be synthesized as shown in following Scheme 3.

Scheme 3

(wherein Y, V, T and R are as described above)

Namely, available or synthesizable general formula (39) is reacted for 1 to 5 hours at −78 to 25° C. in a suitable solvent, for example, ether, tetrahydrofuran or the like in the presence of chloroform, using an organic base, for example, potassium ter-butoxide or the like to convert to general formula (40), and these are reacted with compounds represented by general formula (12)

(12)

(wherein Y, T and V are as described above), for 0.5 to 24 hours at 20 to 160° C. without solvent or in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like to convert to general formula (41).

These are reacted for 10 to 30 minutes at 20 to 80° C. in a suitable solvent, for example, water, acetic acid, mixed solvent thereof or the like, using a suitable reducing agent, for example, titanium trichloride or the like, and then brought to alkaline with a suitable alkali, for example, potassium hydroxide, sodium hydroxide, lithium hydroxide or the like, thus allowing to convert to general formula (23).

Moreover, compounds, A being single bond among compounds represented by the general formula (25), can be synthesized through publicly known process (Scheme 4).

Scheme 4

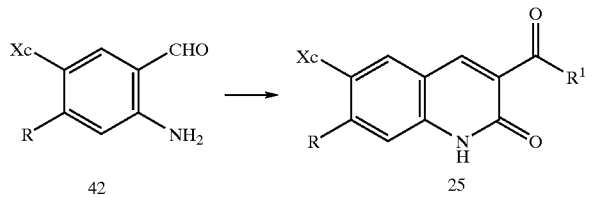

(wherein R, $R^1$ and Xc are as described above)

Namely, they can be synthesized by reacting general formula (42) with malonic esters, for example, diethyl malonate or the like, for 2 to 24 hours at 25 to 100° C. in a suitable solvent, for example, alcohol such as ethanol or methanol, tetrahydrofuran, N,N-dimethylformamide or the like in the presence of a suitable base, for example, sodium ethoxide, potassium ter-butoxide, potassium hydroxide or the like.

Here, compounds, R being nitro group among compounds represented by general formula (42), can be synthesized through processes shown in following Scheme 5.

Scheme 5

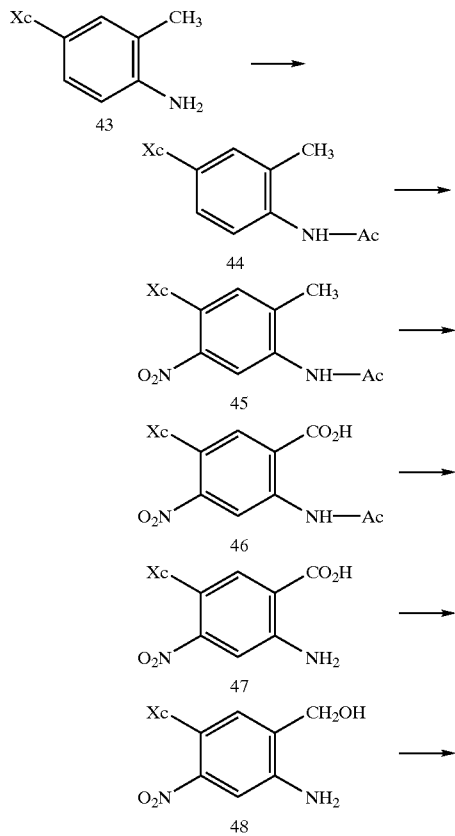

-continued

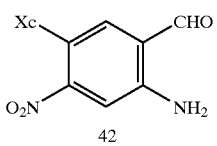

(wherein Xc is as described above)

Namely, available or synthesizable general formula (43) are acetylated with acetic anhydride at room temperature to convert to general formula (44), these are reacted for 0.5 to 2 hours at −10 to 80° C. in a suitable solvent, for example, nitromethane, acetic acid, sulfuric acid or the like, using a suitable nitrating agent, for example, concentrated nitric acid, fuming nitric acid, potassium nitrate, acetyl nitrate or the like to convert to general formula (45), and these are reacted for 1 to 15 hours at 0 to 120° C. in a suitable solvent, for example, water, acetone or the like, using a suitable oxidizing agent, for example, potassium permanganate, sodium periodate or the like to convert to general formula (46). These are hydrolyzed for 1 to 10 hours at 20 to 100° C. in a suitable solvent, for example, water, ethanol, methanol, mixed solution thereof or the like, using a suitable base, for example, sodium hydroxide, potassium hydroxide or the like, or they are hydrolyzed for 1 to 10 hours at 20 to 100° C. in a suitable solvent, for example, water, ethanol, methanol or the like or mixed solution thereof, using a suitable acid, for example, hydrochloric acid, hydrobromic acid or the like, thereby converting to general formula (47). Next, general formula (47) are reacted for 1 to 10 hours at 20 to 150° C. in a suitable solvent, for example, ether, tetrahydrofuran, dioxane or the like, using a suitable reducing agent, for example, borane complex such as borane-tetrahydrofuran complex, borane-dimethyl sulfide complex, borane-pyridine complex or the like to convert to general formula (48), and successively these are reacted for 1 to 24 hours at 20 to 100° C. in a suitable solvent, for example, chloroform, methylene chloride, tetrahydrofuran or the like, using a suitable oxidizing agent, for example, manganese dioxide or the like, thus allowing to convert to general formula (42).

Moreover, compounds, R being nitro group among compounds represented by the general formula (26), can be synthesized through processes shown in following Scheme 5.

Scheme 6

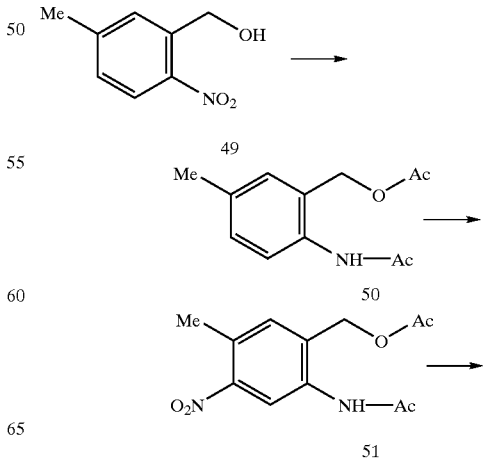

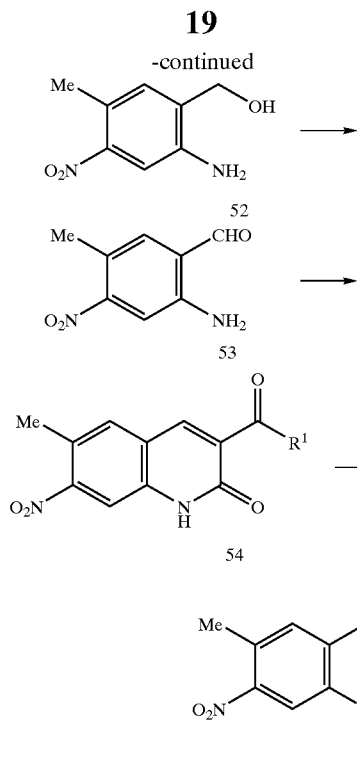

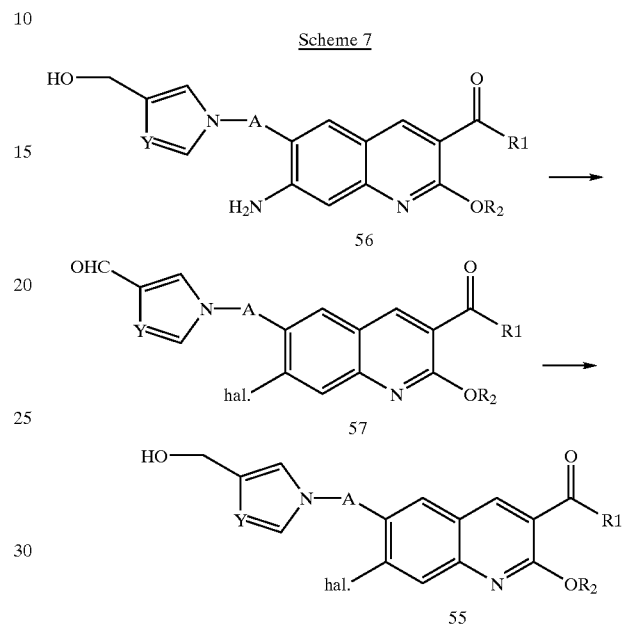

(wherein $R^1$ and $R^2$ are as described above)

Namely, available general formula (49) is acetylated with acetic anhydride at room temperature to convert to general formula (50), this is reacted for 0.5 to 2 hours at −10 to 80° C. in a suitable solvent, for example, nitromethane, acetic acid, sulfuric acid or the like, using a suitable nitrating agent, for example, concentrated nitric acid, fuming nitric acid, potassium nitrate, acetyl nitrate or the like to convert to general formula (51), and this is hydrolyzed for 1 to 10 hours at 20 to 100° C. in a suitable solvent, for example, water, ethanol, methanol, mixed solution thereof or the like, using a suitable base, for example, sodium hydroxide, potassium hydroxide or the like, or it is hydrolyzed for 1 to 10 hours at 20 to 100° C. in a suitable solvent, for example, water, ethanol, methanol or the like or mixed solution thereof, using a suitable acid, for example, hydrochloric acid, hydrobromic acid or the like, thereby converting to general formula (52). Next, the general formula (52) is reacted for 1 to 10 hours at 20 to 100° C. in a suitable solvent, for example, chloroform, methylene chloride, tetrahydrofuran, benzene, water or the like, using a suitable oxidizing agent, for example, manganese dioxide or the like to convert to general formula (53). This general formula (53) is reacted with malonic esters, for example, diethyl malonate or the like, for 2 to 24 hours at 25 to 100° C. in a suitable solvent, for example, alcohol such as ethanol or methanol, tetrahydrofuran, N,N-dimethylformamide or the like in the presence of a suitable base, for example, sodium ethoxide, potassium ter-butoxide, potassium hydroxide or the like to convert to general formula (54), and then these are reacted with alkyl halide, for example, methyl iodide or the like, or aralkyl halide, for example, 4-methoxybenzyl chloride or the like, for 2 to 10 hours at 20 to 120° C. in a suitable solvent, for example, benzene, toluene, chloroform, methylene chloride, tetrahydrofuran or the like, using a suitable silver catalyst, for example, silver oxide, silver carbonate or the like, thus allowing to convert to the general formula (26).

Moreover, compounds represented by the general formula (54) can also be reacted for 2 to 6 hours at 0 to 120° C. in a suitable solvent, for example, benzene, toluene, chloroform, methylene chloride, tetrahydrofuran or the like, using borate, for example, tetramethyloxonium borate or the like to convert to the general formula (26).

Moreover, compounds represented by a general formula (55), R being halogen, V being methylene and $T^1$ being hydroxyl group among compounds represented by the general formula (10), can also be synthesized through processes shown in following Scheme 7.

(wherein $R^1$ and $R^2$ are as described above, and hal. denotes a halogen atom)

Namely, compounds represented by general formula (56) are reacted with a suitable nitrite, for example, sodium nitrite, nitrous ester, for example, t-butyl nitrite or the like, and halide, for example, potassium chloride or potassium bromide or copper (I or II) halide, for example, copper chloride, copper bromide or copper iodide, for 1 to 8 hours at 20 to 50° C. in a suitable solvent, for example, dimethyl sulfoxide, acetonitrile, acetic acid, water, mixed solvent thereof or the like to convert to compounds represented by general formula (57), and these are reduced at 0 to 100° C. in a suitable solvent, for example, ethanol, methanol, isopropanol, water, mixed solution thereof or the like, using a suitable reducing agent, for example, sodium borohydride or the like, thus allowing to synthesize.

Moreover, compounds represented by the general formula (55) can also be obtained directly by reacting compounds represented by the general formula (56) with a suitable nitrite, for example, sodium nitrite, nitrous ester, for example, t-butyl nitrite or the like, and halide, for example, potassium chloride or potassium bromide or copper (I or II) halide, for example, copper chloride, copper bromide or copper iodide, for 0.5 to 2 hours at 0 to 50° C. in a suitable solvent, for example, dimethyl sulfoxide, acetonitrile, acetic acid, water, mixed solvent thereof or the like.

Moreover, compounds represented by the general formula (56) can be obtained by hydrogenating compounds represented by general formula (58), R being nitro group, V being methylene and $T^1$ being hydroxyl group among compounds represented by the general formula (10), for 2 to 24 hours at 25 to 80° C. and at atmospheric pressure to 5 atm (507 KPa) in a suitable solvent, for example, ethanol, methanol, acetic acid, mixed solution thereof or the like in the presence of a suitable catalyst, for example, palladium on carbon, platinum oxide or the like (Scheme 8).

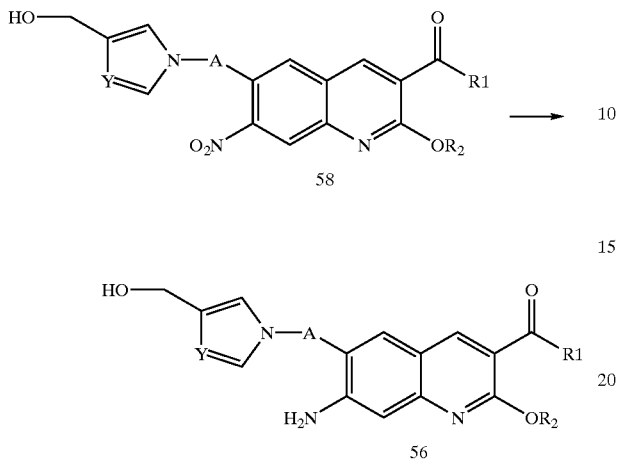

(wherein A, Y, $R^1$ and $R^2$ are as described above)

Moreover, compounds represented by the general formula (56) can also be obtained by reacting compounds represented by general formula (58) with a suitable reducing agent, for example, reducing iron, tin, tin chloride (II), titanium trichloride or the like for 2 to 24 hours at 25 to 100° C. in a suitable solvent, for example, ethanol, methanol, acetic acid, hydrochloric acid, water, mixed solution thereof or the like.

Describing the examples of the inventive compounds, the invention will be illustrated in more detail.

EXAMPLE 1

Ethyl 2-ethoxy-6-(4-(hydroxymethyl)imidazole-1-yl)-7-nitroquinoline-3-carboxylate

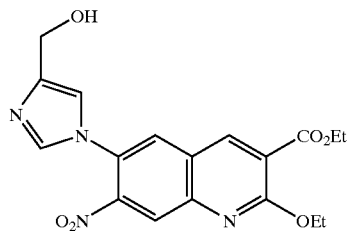

To a solution of ethyl 2-ethoxy-6-fluoro-7-nitroquinoline-3-carboxylate (1.00 g, 3.24 mmol) in acetonitrile (10 ml) were added 4-(hydroxymethyl)imidazole hydrochloride (2.18 g, 16.2 mmol) and successively triethylamine (3 ml), and the mixture was stirred for 16 hours at 120° C. in a sealed tube under shading. After cooling, solvent was distilled off and the residue was submitted to silica gel column chromatography [dichloromethane-methanol(50:1→20:1)] under shading to obtain 583 mg of title compound as light brown powder. Yield 47%. 1H-NMR(DMSO-d6, δ): 1.35 (3H,t,J=7.3 Hz), 1.42(3H,t,J=7.3 Hz), 4.38 (2H,q,J=7.3 Hz), 4.42(2H,d,J=6.8 Hz), 4.58(2H,d,J=7.3 Hz), 5.05(1H, t,J=5.4 Hz), 7.27(1H,s), 7.88(1H,s), 8.39(1H,s), 8.50(1H,s), 8.87 (1H,s).

EXAMPLE 2

1,2-Dihydro-7-nitro-2-oxo-6-(4-((phenylcarbamoyloxy)methyl)imidazole-1-yl) quinoline-3-carboxylic acid

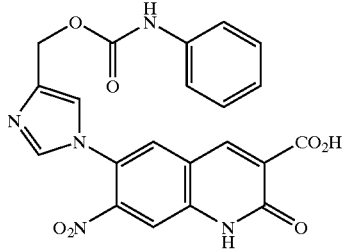

To a solution of the compound of Example 1 (50.0 mg, 129 μmol) in dichloromethane (2 ml) was added phenyl isocyanate (46.2 mg, 388 μmol), and the mixture was stirred overnight at room temperature. Diisopropyl ether was added to the reaction mixture, and the precipitated crystals were collected by filtration and air-dried. These were dissolved into acetic acid (5 ml) and concentrated hydrochloric acid (1 ml) was added, which was stirred overnight at room temperature. The reaction mixture was concentrated under reduced pressure. The residue was washed with water and ethyl acetate in sequence and then air-dried, thereby obtaining 41.0 mg of title compound as yellow powder. Yield 71%.

mp>300° C.

HR-FAB+: 450.1034 (−1.6 mmu).

EXAMPLES 3 THROUGH 14

Through the process similar to Example 2, compounds listed in following Table 1 were obtained.

TABLE 1

| Example | R |
|---------|---|
| 3 | Ph-2-Br |
| 4 | Ph-3-Br |
| 5 | Ph-4-Br |
| 6 | Ph-2-F |
| 7 | Ph-4-F |
| 8 | Ph-2,4-$F_2$ |
| 9 | Ph-4-OMe |
| 10 | Ph-4-Me |
| 11 | Ph-2-$CF_3$ |
| 12 | Ph-3-$CO_2Et$ |
| 13 | Ph-4-$CO_2Et$ |
| 14 | Bn |

EXAMPLE 3 mp>300° C.

HR-FAB+: 528.0127 (−2.8 mmu).

EXAMPLE 4 mp 182–184° C.
Anal. Calcd. for $C_{21}H_{14}BrN_5O_6.H_2O$: C, 46.17; H, 2.95; N, 12.82. Found: C, 46.08; H, 2.72; N, 12.59.
HR-FAB+: 528.0176 (+2.1 mmu).

EXAMPLE 5 mp 281–283° C. (decomposition).
HR-FAB+: 528.0181 (+2.6 mmu).

EXAMPLE 6 mp 226–228° C.
Anal. Calcd. for $C_{21}H_{14}FN_5O_7.HCl$: C, 50.06; H, 3.00; N, 13.90. Found: C, 49.68; H, 2.96; N, 13.77.
HR-FAB−: 466.0777 (−2.2 mmu).

EXAMPLE 7 mp 218–220° C.
Anal. Calcd. for $C_{21}H_{14}FN_5O_7.H2O$: C, 51.97; H, 3.32; N, 14.43. Found: C, 51.92; H, 3.01; N, 14.45.
HR-FAB+: 468.0977 (+2.1 mmu).

EXAMPLE 8 mp>300° C.
Anal. Calcd. for $C_{21}H_{13}F_2N_5O_7$: C, 51.97; H, 2.70; N, 14.43. Found: C, 51.74; H, 2.66; N, 14.27.
HR-FAB+: 484.0733 (+2.8 mmu).

EXAMPLE 9 mp 195–197° C.
Anal. Calcd. for $C_{22}H_{17}N_5O_8.7/5H_2O$: C, 52.36; H, 3.95; N, 13.88. Found: C, 52.66; H, 3.78; N, 13.72.
HR-FAB+: 480.1167 (+1.2 mmu).

EXAMPLE 10 mp 209–211° C.
Anal. Calcd. for $C_{22}H_{17}N_5O_7.HCl$: C, 52.86; H, 3.63; N, 14.01. Found: C, 53.21; H, 3.79; N, 14.03.
HR-FAB+: 464.1227 (+2.1 mmu).

EXAMPLE 11 mp 176–178° C.
Anal. Calcd. for $C_{22}H_{14}F_3N_5O_7.HCl.5/2H_2O$: C, 44.12; H, 3.19; N, 11.69. Found: C, 44.19; H, 2.91; N, 11.58.
HR-FAB+: 516.0767 (0.0 mmu).

EXAMPLE 12 mp 173–175° C.
HR-FAB+: 520.1155 (+5.0 mmu).

EXAMPLE 13 mp 260–262° C. (decomposition).
HR-FAB+: 520.1120 (+1.5 mmu).

EXAMPLE 14 mp 213–215° C.
HR-FAB+: 464.1232 (+2.6 mmu).

EXAMPLE 15

6-(4-(((3-Carboxyphenyl)carbamoyloxy)methyl) imidazole-1-yl)-1,2-dihydro-7-nitro-2-oxoquinoline-3-carboxylic acid To a suspension of the compound of Example 12 (8.00 mg, 15.3 μmol) in water (1 ml) was added 1 mol/L aqueous solution (1 ml) of lithium hydroxide, and the mixture was stirred for 30 minutes at 80° C. After cooling with ice, the reaction mixture was brought to pH4 with 3 mol/L hydrochloric acid. The precipitated crystals were collected by filtration, washed with water and then air-dried, thereby obtaining 5.00 mg of title compound as yellow powder. Yield 66%.

mp>300° C.

HR-FAB−: 492.0802 (+1.0 mmu).

EXAMPLE 16

6-(4-(((4-Carboxyphenyl)carbamoyloxy)methyl) imidazole-1-yl)-1,2-dihydro-7-nitro-2-oxoquinoline-3-carboxylic acid Using the compound of Example 13 (17.0 mg, 32.6 μmol) and through the process similar to Example 15, 12.0 mg of title compound were obtained as yellow powder. Yield 75%.

mp>300° C.

HR-FAB−: 492.0793 (+0.1 mmu).

EXAMPLE 17

Ethyl 1,2-dihydro-6-(4-(hydroxymethyl)imidazole-1-yl)-2-oxo-7-trifluoromethylquinoline-3-carboxylate

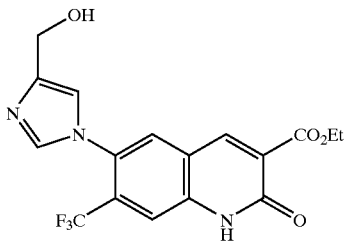

To a solution of diethyl malonate (2.47 g, 15.4 mmol) in absolute ethanol (10 ml) was added dropwise 1.4 mol/L sodium ethoxide-ethanol solution (15.4 ml, 21.6 mmol), and the mixture was stirred for 15 minutes at room temperature. This was added to a solution of 5-(4-(hydroxymethyl) imidazole-1-yl)-4-trifluoromethylanthranylaldehyde (1.46 g, 5.12 mmol) in absolute ethanol (50 ml) and the mixture was stirred for 6 hours at room temperature. After allowed to stand statically overnight, the precipitated crystals were collected by filtration, washed with ethanol, and then dried under reduced pressure. The crystals obtained were suspended into water and the pH value was brought to 4 with 3 mol/L hydrochloric acid under cooling with ice. The precipitated crystals were collected by filtration, washed with water, and then air-dried, thereby obtaining 768 mg of title compound as colorless powder. Yield 39%.

1H-NMR(DMSO-d6, δ): 1.30(3H,t,J=7.3 Hz), 4.30(2H, q,J=7.3 Hz), 4.42 (2H,d,J=7.3 Hz), 5.02(1H,t,J=7.3 Hz), 7.20(1H,s), 7.74(1H,s), 7.79 (1H,s), 8.09(1H,s), 8.56(1H,s), 12.49(1H,brs).

EXAMPLE 18

Ethyl 1,2-dihydro-6-(4-(((4-ethoxycarbonylphenyl) carbamoyloxy)methyl)imidazole-1-yl)-2-oxo-7-trifluoromethylquinoline-3-carboxylate

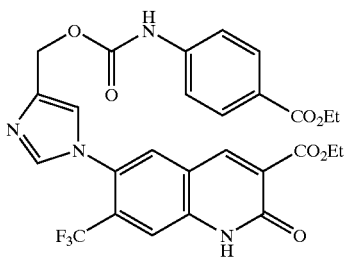

To a suspension of the compound of Example 17 (768 mg, 2.01 mmol) in ethyl acetate (30 ml) was added ethyl 4-isocyanatobenzoate (769 mg, 4.02 mmol), and the mixture was refluxed for 48 hours. After cooling with ice, the precipitated crystals were collected by filtration, washed with ethyl acetate, and then dried under reduced pressure, thereby obtaining 1.13 g of title compound as colorless powder. Yield 98%.

1H-NMR(DMSO-d6, δ): 1.30(3H,t,J=7.3 Hz), 4.28(2H, q,J=7.3 Hz), 4.30 (2H,q,J=7.3 Hz), 5.11(2H,s), 7.53(1H,s), 7.61(2H,d,J=8.8 Hz), 7.79 (1H,s), 7.87(1H,s), 7.89(2H,d,J= 8.8 Hz), 8.10(1H,s), 8.56(1H,s), 10.21(1H,s), 12.49(1H,brs).

EXAMPLE 19

6-(4-(((4-Carboxyphenyl)carbamoyloxy)methyl) imidazole-1-yl)-1,2-dihydro-2-oxo-7-trifluoromethylquinoline-3-carboxylic acid

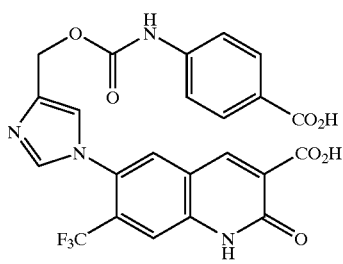

To a suspension of the compound of Example 18 (1.13 g, 1.97 mmol) in ethanol (30 ml) was added 1 mol/L aqueous solution of lithium hydroxide (9.26 ml, 9.26 mmol) and successively water (15 ml), and, after stirring for 4 hours at room temperature, the mixture was allowed to stand statically overnight. After stirring for 16 hours at 30° C., ice water was added to the reaction mixture and the insolubles were filtered off. Then, the pH value was brought to 4 with 3 mol/L hydrochloric acid and solvent was distilled off. Water was added to the residue obtained, the precipitated crystals were collected by filtration, washed with water, and then dried under reduced pressure. After the powder obtained was suspended into water (40 ml), 1 mol/L aqueous solution of lithium hydroxide (9.26 ml, 9.26 mmol) was added and the mixture was stirred for 30 minutes at 50° C. Ice water was added to the reaction mixture, the insolubles were filtered off, then the pH value was brought to 4 with 3 mol/L hydrochloric acid, and solvent was distilled off. Water was added to the residue obtained, the precipitated crystals were collected by filtration, washed with water, and then dried under reduced pressure, thereby obtaining 757 mg of title compound as pale yellow powder.

Yield 71%.

mp 218–220° C.

Anal. Calcd. for $C_{23}H_{15}F_3N_4O_7 \cdot 3/2H_2O$: C, 50.84; H, 3.33; N, 10.31. Found: C, 50.59; H, 3.22; N, 10.13.

HR-FAB+: 517.0961 (−1.0 mmu).

EXAMPLE 20

Ethyl 1,2-dihydro-6-(3-formylpyrrole-1-yl)-2-oxo-7-trifluoromethylquinoline-3-carboxylate

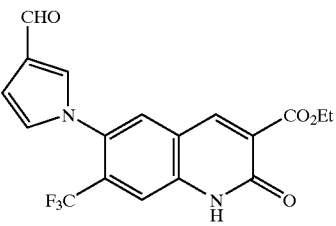

To a solution of ethyl 6-amino-1,2-dihydro-2-oxo-7-trifluoro-methylquinoline-3-carboxylate (93.0 mg, 310 μmol) in acetic acid (6 ml) was added dropwise 2,5-dimethoxytetrahydrofuran-3-aldehyde (52.8 μl, 372 μmol) at 50° C., and the mixture was stirred for 1 hour at the same temperature. The reaction mixture was poured into water (60 ml), which was extracted with ethyl acetate. After dried the extract over anhydrous sodium sulfate, solvent was distilled off. A small quantity of ethyl acetate was added to the residue obtained, the insolubles were filtered off, and solvent was distilled off. The residue obtained was submitted to separating thin layer chromatography [ethyl acetate-hexane=2:1] to obtain 14.5 mg of title compound as pale yellow powder. Yield 12%.

1H-NMR(CDCl$_3$, δ): 1.46(3H,t,J=7.3 Hz), 4.48(2H,q,J= 7.3 Hz), 6.82 (1H,q,J=1.5 Hz), 6.86(1H,s), 7.45(1H,s), 7.78 (1H,s), 7.88(1H,s), 8.55(1H,s), 9.87(1H,s), 12.33(1H,brs).

EXAMPLE 21

Ethyl 1,2-dihydro-6-(3-(((4-ethoxycarbonylphenyl)aminocarbonylamino)methyl)pyrrole-1-yl)-2-oxo-7-trifluoromethylquinoline-3-carboxylate

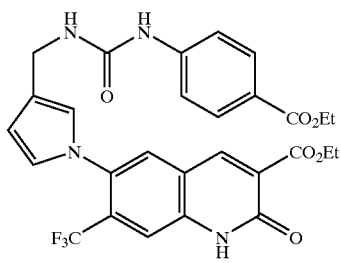

To a solution of the compound of Example 20 (25.6 mg, 67.7 μmol) in ethanol (2 ml) were added hydroxylamine hydrochloride (9.38 mg, 135 μmol) and successively sodium acetate (11.1 mg, 135 μmol), and the mixture was refluxed for 3 hours. After cooling, the insolubles were filtered off and solvent was distilled off. The residue obtained was dissolved into ethanol (6 ml) and then 10% palladium-carbon (3.00 mg) and successively concentrated hydrochloric acid (0.2 ml) were added, which was stirred for 2 hours at room temperature under hydrogen atmosphere (4 atm, 392 KPa). Catalyst was filtered off using celite and solvent was distilled off. After the residue obtained was dissolved into N,N-dimethylformaldehyde (2 ml), ethyl 4-isocyanatobenzoate (15.5 mg, 81.2 μmol) and successively triethylamine (14.2 μl, 102 μmol) were added and the mixture was stirred for 1 hour at 60° C. Water was added to the residue obtained by distilling off solvent, which was extracted with ethyl acetate. After dried the extract over anhydrous sodium sulfate, solvent was distilled off. A small quantity of ethyl acetate was added to the residue obtained. The crystals were collected by filtration, washed with ethyl acetate, and then air-dried, thereby obtaining 23.2 mg of title compound as greenish yellow powder. Yield 60%.

1H-NMR(DMSO-d6, δ): 1.30(6H,t,J=6.8 Hz), 4.19(2H,d,J=4.9 Hz), 4.26 (2H,q,J=6.9 Hz), 4.30(2H,q,J=6.9 Hz), 6.23(1H,t,J=2.0 Hz), 6.50(1H, brs), 6.88(2H,s), 7.52(2H,d,J=8.8 Hz), 7.75(1H,s), 7.83(2H,d,J=8.8 Hz), 8.00(1H,s), 8.55(1H,s), 8.91(1H,s).

EXAMPLE 22

6-(3-(((4-Carboxyphenyl)aminocarbonylamino)methyl)pyrrole-1-yl)-1,2-dihydro-2-oxo-7-trifluoromethylquinoline-3-carboxylate

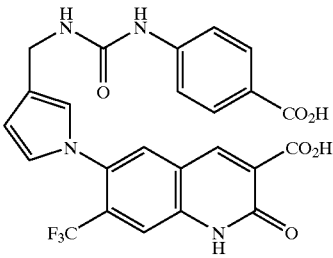

To a solution of the compound of Example 21 (21.7 mg, 38.0 μmol) in ethanol (1 ml) was added 1 mol/L aqueous solution of potassium hydroxide (152 μl, 152 μmol), and the mixture was refluxed for 2 hours. After cooling, solvent was distilled off and the residue was dissolved into a small quantity of water, then the pH value was brought to 4 with 4 mol/L hydrochloric acid. The precipitated crystals were collected by filtration, washed with water, and then air-dried, thereby obtaining 6.20 mg of title compound as yellowish brown powder. Yield 32%.

mp 218–220° C.

HR-FAB–: 513.1024 (+0.2 mmu).

EXAMPLE 23

Ethyl 1,2-dihydro-2-oxo-6-(4-((phenylcarbamoyloxy)methyl)imidazole-1-yl)-7-trifluoromethylquinoline-3-carboxylate

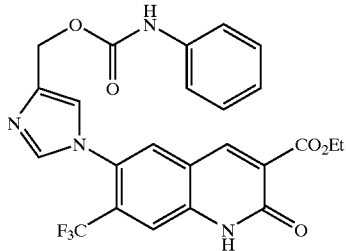

Using the compound of Example 17 (200 mg, 525 μmol) and phenyl isocyanate (93.9 mg, 0.788 mmol), and through the process similar to Example 18, 234 mg of title compound were obtained as colorless powder. Yield 89%.

1H-NMR(DMSO-d6, δ): 1.30(3H,t,J=7.3 Hz), 4.30(2H,q,J=7.3 Hz), 5.07 (2H,s), 6.98(1H,t,J=7.3 Hz), 7.27(2H,t,J= 7.3 Hz), 7.47(2H,d,J=7.3 Hz), 7.51(1H,s), 7.79 (1H,s), 7.86 (1H,s), 8.10(1H,s), 8.56(1H,s), 9.76(1H,s), 12.48(1H,brs).

EXAMPLE 24

1,2-Dihydro-2-oxo-6-(4-((phenylcarbamoyloxy)methyl)imidazole-1-yl)-7-trifluoromethylquinoline-3-carboxylic acid

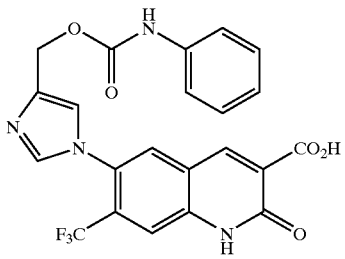

Using the compound of Example 23 (100 mg, 200 μmol) and through the process similar to Example 19, 87.0 mg of title compound were obtained as white powder. Yield 92%.

mp 178–180° C.

HR-FAB-: 471.0926 (+1.0 mmu).

EXAMPLE 25

6-(4-(((2-Bromophenyl)carbamoyloxy)methyl)imidazole-1-yl)-1,2-dihydro-2-oxo-7-trifluoromethylquinoline-3-carboxylic acid

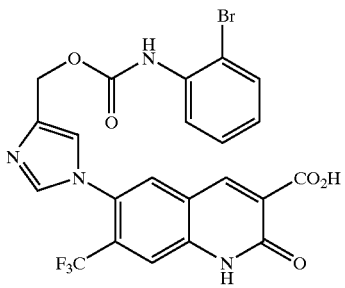

To a suspension of the compound of Example 17 (100 mg, 262 μmol) in ethyl acetate (3 ml) was added 2-bromophenyl isocyanate (104 mg, 524 μmol), and the mixture was refluxed for 24 hours. After cooling, the precipitated crystals were collected by filtration, washed with ethyl acetate, and then dried under reduced pressure. These were suspended into ethanol (3 ml), 1 mol/L aqueous solution of lithium hydroxide (903 μl) and successively water (3 ml) were added, and the mixture was stirred for 75 minutes at 50° C. Ice water was added to the reaction mixture, the insolubles were filtered off. then the pH value was brought to 4 with 3 mol/L hydrochloric acid. The precipitated crystals were collected by filtration, washed with water, and then dried under reduced pressure, thereby obtaining 55.0 mg of title compound as colorless powder. Yield 34%.

mp 145–147° C.

Anal. Calcd. for $C_{22}H_{14}BrF_3N_4O_5 \cdot H_2O$: C, 46.41; H, 2.83; N, 9.84. Found: C, 46.20; H, 2.57; N, 9.57.

HR-FAB-: 549.0064 (+4.3 mmu).

EXAMPLES 26 THROUGH 32

Using the compound of Example 17 and through the process to Example 25, compounds listed in following Table 2 were obtained

TABLE 2

| Example | R |
|---|---|
| 26 | Ph-3-Br |
| 27 | Ph-4-Br |
| 28 | Ph-2-F |
| 29 | Ph-2-$CF_3$ |
| 30 | Ph-4-Me |
| 31 | Ph-4-OMe |
| 32 | Bn |
| 33 | Ph-3-$CO_2H$ |

EXAMPLE 26 mp 161–163° C.

HR-FAB-: 549.0026 (+0.5 mmu).

EXAMPLE 27 mp 175–177° C.

Anal. Calcd. for $C_{22}H_{14}BrF_3N_4O_5 \cdot 1.2H_2O$: C, 46.12; H, 2.89; N, 9.78. Found: C, 45.82; H, 2.59; N, 9.53.

HR-FAB-: 549.0029 (+0.8 mmu).

EXAMPLE 28 mp 155–157° C.

HR-FAB-: 489.0822 (+0.0 mmu).

EXAMPLE 29 mp 156–158° C.

Anal. Calcd. for $C_{23}H_{14}F_6N_4O_5 \cdot 1.2H_2O$: C, 49.15; H, 2.94; N, 9.97. Found: C, 49.06; H, 2.73; N, 9.92.

HR-FAB-: 538.0809 (+1.9 mmu).

EXAMPLE 30 mp 168–170° C.

Anal. Calcd. for $C_{23}H_{17}F_3N_4O_5 \cdot 1.5H_2O$: C, 53.81; H, 3.93; N, 10.91. Found: C, 53.99; H, 3.64; N, 10.90.

HR-FAB-: 485.1058 (-1.5 mmu).

EXAMPLE 31 mp 176–178° C.

HR-FAB-: 501.1055 (+3.3 mmu).

EXAMPLE 32 mp 169–171° C.

Anal. Calcd. for $C_{23}H_{17}F_3N_4O_5 \cdot 1.5H_2O$: C, 53.81; H, 3.93; N, 10.91. Found: C, 53.57; H, 3.80; N, 10.79.

HR-FAB-: 485.1086 (+1.4 mmu).

EXAMPLE 33 mp 282–284° C.

HR-FAB-: 515.0836 (+2.2 mmu).

EXAMPLE 34

Ethyl 7-chloro-2-ethoxy-6-(4-formylimidazole-1-yl)quinoline-3-carboxylate

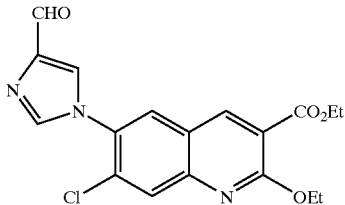

To a solution of the compound of Example 1 (2.06 g, 5.3 mmol) in ethanol (30 ml) were added acetic acid (30 ml) and successively 10% palladium-carbon (206 mg) to submit to hydrogenating reaction at ambient temperature under ambient pressure. After completion of the reaction, catalyst was filtered off using celite and then solvent was distilled off. The powder obtained was suspended into acetonitrile (30 ml) and added to a solution of cupric chloride (1.23 g, 9.18 mmol) and t-butyl nitrite (947 mg, 9.18 mmol) in acetonitrile (70 ml). The mixture was stirred for 8 hours at room temperature and then refluxed for 8 hours. After cooling, ethyl acetate was added to the reaction mixture and the insolubles were filtered off. The organic layer was washed with saturated brine, dried over anhydrous magnesium sulfate, and then solvent was distilled off. The residue obtained was submitted to silica gel column chromatography [hexane:ethyl acetate=1:3→1:5] to obtain 2.11 g of title compound as pale yellow powder. Yield 92%.

1H-NMR(DMSO-d6, δ): 1.34(3H,t,J=6.8 Hz), 1.41(3H,t,J=6.8 Hz), 4.36 (2H,q,J=6.8 Hz), 4.55(2H,q,J=6.8 Hz), 8.14(1H,s), 8.23(1H,s), 8.47 (1H,s), 8.81(1H,s), 9.86(1H,s).

EXAMPLE 35

Ethyl 7-chloro-2-ethoxy-6-(4-(hydroxymethyl)imidazole-1-yl)quinoline-3-carboxylate

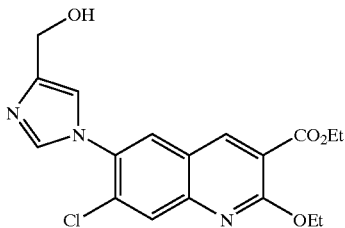

To a solution of the compound of Example 34 (1.91 g, 5.11 mmol) in ethanol (30 ml) was added sodium borohydride (96.8 mg, 2.56 mmol), and the mixture was stirred for 6 hours at room temperature. After concentrated the reaction mixture, the residue obtained was washed with water and then dried under reduced pressure, thereby obtaining 740 mg of title compound as light brown powder. Yield 39%.

1H-NMR(DMSO-d6, δ): 1.34(3H,t,J=6.8 Hz), 1.40(3H,t,J=6.8 Hz), 4.35 (2H,q,J=6.8 Hz), 4.44(2H,d,J=5.4 Hz), 4.54(2H,q,J=6.8 Hz), 5.03(1H, t,J=5.4 Hz), 7.33(1H,s), 7.88 (1H,s), 8.08(1H,s), 8.26(1H,s), 8.80 (1H, s).

EXAMPLE 36

Ethyl 7-chloro-1,2-dihydro-6-(4-(hydroxymethyl)imidazole-1-yl)-2-oxoquinoline-3-carboxylate

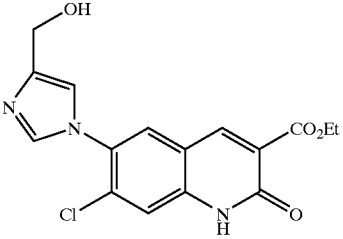

To a solution of the compound of Example 35 (740 mg, 1.97 mmol) in ethanol (50 ml) was added concentrated hydrochloric acid (5 ml), and the mixture was refluxed for 16 hours, attaching Dean-Stark refluxing apparatus equipped with molecular sieves 4A. After cooling, the precipitated crystals were collected by filtration, washed with ethanol and then dried under reduced pressure, thereby obtaining 994 mg of title compound as light brown powder. The yield was quantitative.

1H-NMR(DMSO-d6, δ): 1.30(3H,t,J=7.3 Hz), 4.29(2H,q,J=7.3 Hz), 4.56 (2H,s), 7.61(1H,s), 7.74(1H,s), 8.23(1H,s), 8.53(1H,s), 9.03 (1H, brs), 12.45(1H,s).

EXAMPLE 37

Ethyl 7-chloro-1,2-dihydro-2-oxo-6-(4-((phenylcarbamoyloxy)methyl)imidazole-1-yl)quinoline-3-carboxylate

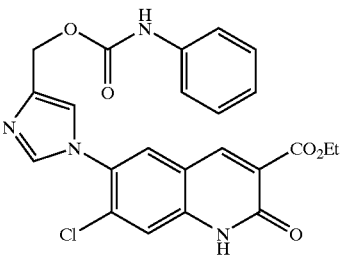

To a suspension of the compound of Example 36 (100 mg, 288 μmol) in ethyl acetate (5 ml) were added phenyl isocyanate (68.6 mg, 576 μmol) and successively triethylamine (58.3 mg, 576 μmol), and the mixture was refluxed for 24 hours. After cooling, the precipitated crystals were collected by filtration, washed with ethyl acetate and water in sequence, and then dried under reduced pressure, thereby obtaining 44.0 mg of title compound as colorless powder. Yield 33%.

1H-NMR(DMSO-d6, δ): 1.30(3H,t,J=7.3 Hz), 4.28(2H,q,J=7.3 Hz), 5.08 (2H,s), 6.98(1H,t,J=7.3 Hz), 7.27(2H,t,J=7.3 Hz), 7.47(2H,d,J=7.3 Hz), 7.53(1H,s), 7.55(1H,s), 7.92 (1H,s), 8.09(1H,s), 8.53(1H,s), 9.76(1H,s), 12.31(1H,brs).

EXAMPLES 38 THROUGH 40

Using the compound of Example 36 and through the process similar to Example 37, compounds listed in following Table 3 were obtained.

TABLE 3

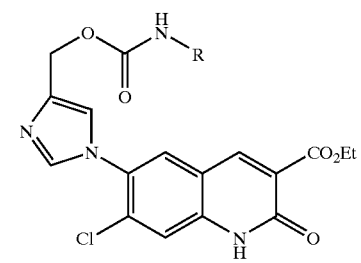

| Examples | R |
|---|---|
| 38 | Ph-2-CF$_3$ |
| 39 | Ph-3-CO$_2$Et |
| 40 | Ph-4-CO$_2$Et |

EXAMPLE 38

1H-NMR(DMSO-d6, δ): 1.30(3H,t,J=6.8 Hz), 4.29(2H, q,J=6.8 Hz), 5.08 (2H,s), 7.15–7.24(3H,m), 7.54(1H,s), 7.63–7.67(1H,m), 7.92(1H,s), 8.10(1H,s), 8.53(1H,s), 9.44 (1H,s), 12.32(1H,s).

EXAMPLE 39

1H-NMR(DMSO-d6, δ): 1.30(3H,t,J=7.3 Hz), 1.31(3H,t, J=6.8 Hz), 4.26–4.33(4H,m), 5.11(2H,s), 7.43(1H,t,J=7.8 Hz), 7.54–7.60(3H,m), 7.69 (1H,d,J=7.8 Hz), 7.92(1H,s), 8.10(1H,s), 8.18(1H,s), 8.53(1H,s), 10.03(1H,s), 12.34(1H, s).

EXAMPLE 40

1H-NMR(DMSO-d6, δ): 1.295(34H,t,J=6.8 Hz), 1.301 (3H,t,J=7.3 Hz), 4.25–4.31(4H,m), 5.12(2H,s), 7.53(1H,s), 7.57(1H,s), 7.60(2H,d,J=8.8 Hz), 7.89(2H,d,J=8.8 Hz), 7.92 (1H,s), 8.09(1H,s), 8.53(1H,s), 10.20(1H,s), 12.31(1H,s).

EXAMPLE 41

7-Chloro-1,2-dihydro-2-oxo-6-(4-((phenylcarbamoyloxy)methyl)imidazole-1-yl) quinoline-3-carboxylic acid

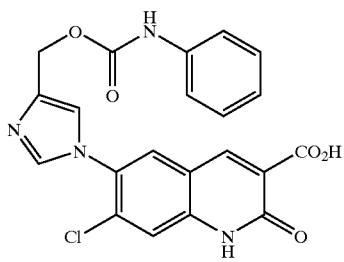

Using the compound of Example 37 (44.0 mg, 94.2 μmol) and through the process similar to Example 19, 36.0 mg of title compound were obtained as white powder. Yield 82%.

mp 180–182° C.

Anal. Calcd. for C$_{21}$H$_{15}$ClN$_4$O$_5$·1.5H$_2$O: C, 54.14; H, 3.89; N, 12.03. Found: C, 54.27; H, 3.77; N, 11.93.

HR-FAB−: 437.0652 (−0.1 mmu).

EXAMPLE 42

7-Chloro-1,2-dihydro-2-oxo-6-((((2-trifluoromethylphenyl)carbamoyloxy)methyl) imidazole-1-yl)quinoline-3-carboxylic acid

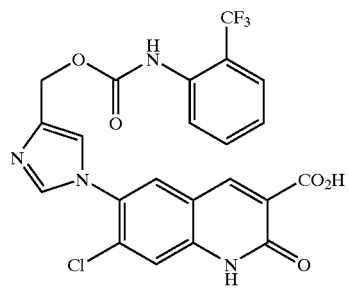

Using the compound of Example 38 (49.0 mg, 91.6 μmol) and through the process similar to Example 19, 21.0 mg of title compound were obtained as white powder. Yield 45%.

mp>300° C.

HR-FAB−: 505.0526 (−0.1 mmu).

EXAMPLE 43

6-((((3-Carboxyphenyl)carbamoyloxy)methyl) imidazole-1-yl)-7-chloro-1,2-dihydro-2-oxoquinoline-3-carboxylic acid

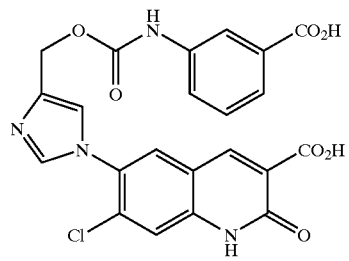

Using the compound of Example 39 (81.0 mg, 150 μmol) and through the process similar to Example 19, 23.0 mg of title compound were obtained as white powder. Yield 30%.

mp 263–265° C. (decomposition).

Anal. Calcd. for C$_{22}$H$_{15}$ClN$_4$O$_7$·1.8H$_2$O: C, 51.28; H, 3.64; N, 10.87. Found: C, 51.27; H, 3.55; N, 10.70.

HR-FAB−: 481.0549 (−0.2 mmu).

EXAMPLE 44

6-((((4-Carboxyphenyl)carbamoyloxy)methyl)
imidazole-1-yl)-7-chloro-1,2-dihydro-2-
oxoquinoline-3-carboxylic acid

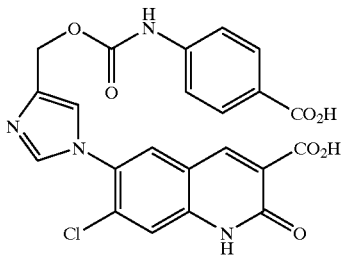

Using the compound of Example 40 (50.0 mg, 92.8 μmol) and through the process similar to Example 19, 33.6 mg of title compound were obtained as white powder. Yield 69%.

mp 249–251° C.

Anal. Calcd. for $C_{22}H_{15}ClN_4O_7 \cdot 2.2H_2O$: C, 50.58; H, 3.74; N, 10.72. Found: C, 50.87; H, 3.89; N, 10.47.

HR-FAB–: 481.0573 (+2.1 mmu).

EXAMPLES 45 AND 46

Using the compound of Example 36 and through the process similar to Example 25, compounds listed in following Table 4 were obtained.

TABLE 4

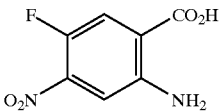

| Example | R |
|---|---|
| 45 | Ph-2-Br |
| 46 | Ph-2-F |

EXAMPLE 45 mp 157–159° C.

Anal. Calcd. for $C_{21}H_{14}BrClN_4O_5 \cdot H_2O$: C, 47.08; H, 3.01; N, 10.46. Found: C, 46.78; H, 2.83; N, 10.29.

HR-FAB–: 514.9753 (–0.5 mmu).

EXAMPLE 46 mp 173–175° C.

Anal. Calcd. for $C_{21}H_{14}ClFN_4O_5 \cdot H_2O$: C, 52.72; H, 3.45; N, 11.71. Found: C, 52.68; H, 3.38; N, 11.56.

HR-FAB–: 455.0559 (+0.1 mmu).

Referential Example 1

4-Fluoro-2-methyl-5-nitroacetanilide

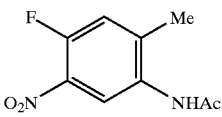

To a solution of 4-fluoro-2-methylacetanilide (46.5 g, 278 mmol) in concentrated sulfuric acid (500 ml) was added dropwise a solution of potassium nitrate (141 g, 1.39 mol) in concentrated sulfuric acid (500 ml) over 2 hours at room temperature. After completion of dropwise addition, the reaction mixture was poured into ice water and the precipitated crystals were collected by filtration. These were washed with water and then air-dried, thereby obtaining 44.5 g of title compound as colorless powder. Yield 75%.

1H-NMR(DMSO-d6, δ): 2.11(3H,s), 2.32(3H,s), 7.50 (1H,d,J=12.7 Hz), 8.34(1H,d,J=7.3 Hz), 9.56(1H,brs).

Referential Example 2

N-Acetyl-5-fluoro-4-nitroanthranilic acid

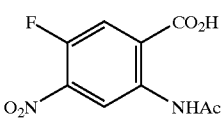

To a solution of potassium permanganate (44.7 g, 283 mmol) and magnesium sulfate (17.0 g, 141 mmol) in water (400 ml) was added the compound of Referential example 1 (20.0 g, 94.3 mmol), and the mixture was refluxed for 30 minutes. Further, a solution of potassium permanganate (44.7 g, 283 mmol) and magnesium sulfate (17.0 g, 141 mmol) in water (100 ml) was added and the mixture was refluxed for 1 hour. While hot, the insolubles were filtered off using celite and, after cooling to room temperature, the pH value of filtrate was adjusted to 4 using 10% hydrochloric acid. After cooling with ice, the precipitated crystals were collected by filtration, washed with water, and then air-dried, thereby obtaining 4.03 g of title compound as white powder. Yield 19%.

1H-NMR(DMSO-d6, δ): 2.15(3H,s), 7.99(1H,d,J=11.2 Hz), 9.09(1H,d, J=6.8 Hz), 10.99(1H,brs).

Referential Example 3

5-Fluoro-4-nitroanthranilic acid

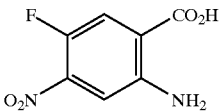

To the compound of Referential example 2 (8.00 g, 33.0 mmol) was added 4 mol/L hydrochloric acid (170 ml), and the mixture was refluxed for 3 hours. After cooling with ice, the precipitated crystals were collected by filtration, washed with water, and then air-dried, thereby obtaining 5.44 g of title compound as brown powder. Yield 82%.

1H-NMR(DMSO-d6, δ): 7.50(1H,d,J=6.3 Hz), 7.70(1H, d,J=12.2 Hz).

Referential Example 4

5-Fluoro-4-nitroanthranilaldehyde

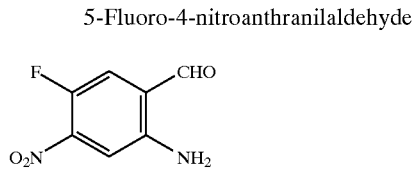

To a solution of Referential example 3 (13.2 g, 66.0 mmol) in tetrahydrofuran (200 ml) was added borane-dimethyl sulfide complex (15.7 ml, 165 mmol), and the mixture was refluxed for 3 hours. After cooling with ice, water (60 ml) was added, which was stirred until bubbling was ceased. Further, concentrated hydrochloric acid (60 ml) was added and the mixture was refluxed for 30 minutes. After cooling, brine was added and the solution was neutralized with saturated aqueous solution of sodium hydrogencarbonate, which was then extracted using ethyl acetate. The organic layer was washed with brine, then dried over anhydrous magnesium sulfate, and solvent was distilled off. Chloroform (100 ml) was added to the residue obtained and manganese dioxide (23.9 g, 275 mmol) was added, which was stirred for 2 hours at room temperature. After the reaction mixture was filtered using celite and silica gel, solvent was distilled off, thereby obtaining 10.8 g of title compound as orange powder. Yield 89%.

1H-NMR(DMSO-d6, δ): 7.33(2H,brs), 7.49(1H,d,J=5.9 Hz), 7.84(1H,d, J=11.2 Hz), 9.91(1H,s).

Referential Example 5

Ethyl 6-fluoro-1,2-dihydro-7-nitro-2-oxoquinoline-3-carboxylate

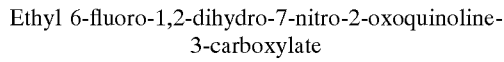

After metallic sodium (805 mg, 35.0 mmol) was dissolved into absolute ethanol (55 ml), diethyl malonate (7.93 ml, 52.5 mmol) was added dropwise, and the mixture was stirred for 15 minutes. This was added to a solution of Referential example 4 (3.23 g, 17.5 mmol) in absolute ethanol (55 ml) and the mixture was stirred for 8 hours. After diluted with ethanol, the reaction mixture was neutralized using acetic acid under cooling with ice. The precipitated crystals were collected by filtration, washed with ethanol, and then air-dried, thereby obtaining 3.87 g of title compound as yellow powder. Yield 79%.

1H-NMR(DMSO-d6, δ): 1.27(3H,t,J=6.8 Hz), 4.20(2H, q,J=6.8 Hz), 7.57 (1H,d,J=11.7 Hz), 7.66(1H,d,J=7.8 Hz), 7.84(1H,s).

Referential Example 6

Ethyl 2-ethoxy-6-fluoro-7-nitroquinoline-3-carboxylate

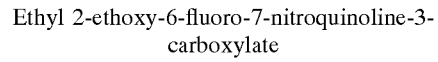

To a suspension of Referential example 5 (11.5 g, 41.0 mmol) in toluene (400 ml) were added silver oxide (I) (19.0 g, 82.1 mmol) and ethyl bromide (7.67 ml, 103 mmol), and the mixture was refluxed for 2 hours. Ethyl bromide (7.67 ml, 103 mmol) was further added, the mixture was refluxed for 2 hours, successively ethyl bromide (9.25 ml, 123 mmol) was added, and the mixture was refluxed for 4 hours. After cooling, the reaction mixture was filtered using celite and celite was washed with ethyl acetate. The organic layers were combined and solvent was distilled off. The residue obtained was purified by means of silica gel column chromatography [hexane-ethyl acetate=7:1→3:1] and then recrystallized from hexane-ethyl acetate to obtain 10.2 g of title compound as pale yellow powder. Yield 81%.

1H-NMR(DMSO-d6, δ): 1.35(3H,t,J=7.3 Hz), 1.40(3H,t, J=6.8 Hz), 4.37 (2H,q,J=7.3 Hz), 4.54(2H,q,J=6.8 Hz), 8.24(1H,d,J=11.7 Hz), 8.48(1H, d,J=6.8 Hz), 8.79(1H,s).

Referential Example 7

4-(Dichloromethyl)-2-fluoro-5-nitrobenzotrifluoride

To a solution of potassium t-butoxide (1.25 g, 11.1 mmol) in tetrahydrofuran (25 ml) was slowly added dropwise a solution of 2-fluoro-5-nitrobenzotrifluoride (1.00 g, 4.78 mmol) and chloroform (599 mg, 5.02 mmol) in tetrahydrofuran (2.5 ml) at −78° C. After stirring for 15 minutes at the same temperature, acetic acid-methanol (1:1, 5 ml) was added and the temperature was raised to room temperature. Ethyl acetate and saturated brine were added to the reaction mixture, which was extracted with ethyl acetate. After washed with brine, the organic layer was dried over anhydrous magnesium sulfate and solvent was distilled off. The residue obtained was submitted to silica gel column chromatography [hexane→hexane-ethyl acetate(300:1)] to obtain 714 mg of title compound as pale yellow liquid. Yield 51%.

1H-NMR(DMSO-d6, δ): 7.73(1H,s), 8.37(1H,d,J=10.7 Hz), 8.50(1H,d,J=6.3 Hz).

Referential Example 8

4-(Dichloromethyl)-2-(4-(hydroxymethyl)imidazole-1-yl)-5-nitro-benzotrifluoride

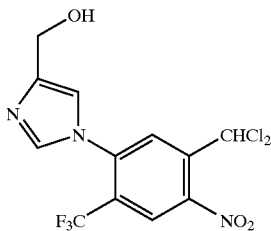

To a solution of the compound of Referential example 7 (5.31 g, 18.2 mmol) in tetrahydrofuran (40 ml) were added 4-(hydroxymethyl)imidazole hydrochloride (4.90 g, 36.4 mmol) and triethylamine (7.37 g, 72.8 mmol), and the mixture was refluxed for 1.5 hours. After cooling, ethyl acetate was added to the reaction mixture, washed with brine, then dried over anhydrous magnesium sulfate and solvent was distilled off. The residue obtained was submitted to silica gel column chromatography [ethyl acetate-hexane (3:1)→ethyl acetate] to obtain 5.15 g of title compound as pale yellow powder. Yield 76%.

1H-NMR(DMSO-d6, δ): 4.44(2H,d,J=4.4 Hz), 5.09(1H, t,J=4.4 Hz), 7.39 (1H,s), 7.78(1H,s), 7.92(1H,s), 8.19(1H,s), 8.59(1H,s).

Referential Example 9

5-(4-(Hydroxymethyl)imidazole-1-yl)-4-trifluoromethyl)anthranil-aldehyde

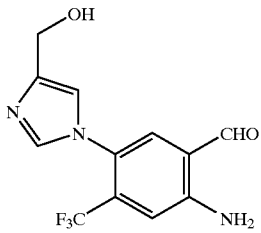

To a solution of the compound of Referential example 8 (500 mg, 1.35 mmol) in acetic acid (10 ml) was added water (1 ml), and 24% aqueous solution of titanium trichloride (4.34 g, 6.75 mmol) was slowly added dropwise at room temperature. After stirring for 15 minutes, the reaction mixture was cooled with ice and made alkaline using 20% aqueous solution of sodium hydroxide. Water and ethyl acetate were added thereto and the insolubles were filtered off using celite. The filtrate was extracted with ethyl acetate. The organic layer was washed with brine, then dried over anhydrous magnesium sulfate and solvent was distilled off. The residue obtained was recrystallized from ethyl acetate to obtain 138 mg of title compound as pale yellow powder. After concentration, the filtrate was submitted to silica gel column chromatography [ethyl acetate→ethyl acetate-methanol(10:1)] to obtain 126 mg additionally. Total yield 264 mg. Yield 69%.

1H-NMR(DMSO-d6, δ): 4.39(2H,d,J=5.9 Hz), 4.97(1H, t,J=5.9 Hz), 7.10 (1H,s), 7.30(1H,s), 7.64(1H,s), 7.67(2H,s), 7.79(1H,s), 9.91(1H,s).

Referential Example 10

4-Methyl-3-nitrobenzotrifluoride

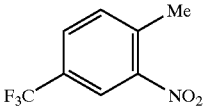

To a solution of 4-methylbenzotrifluoride (18.6 g, 116 mmol) in concentrated sulfuric acid (120 ml) was added dropwise a solution of potassium nitrate (12.9 g, 128 mmol) in concentrated sulfuric acid (60 ml) at room temperature over 15 minutes. After stirring for 2 hours at the same temperature, the reaction mixture was poured into ice water, which was extracted with ethyl acetate, dried over anhydrous sodium sulfate, and solvent was distilled off. The residue obtained was submitted to silica gel column chromatography [hexane-ethyl acetate=8:1] to obtain 22.8 g of title compound as pale yellow liquid. Yield 96%.

1H-NMR(CDCl₃, δ): 2.69(3H,s), 7.52(1H,d,J=8.3 Hz), 7.76(1H,d,J=8.3 Hz), 8.25 (1H,s).

Referential Example 11

2-Methyl-5-trifluoromethylacetanilide

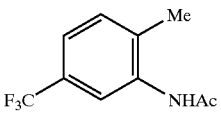

To a solution of the compound of Referential example 10 (22.8 g, 111 mmol) in methanol (300 ml) was added 10% palladium-carbon (containing 51.1% moisture, 2.28 g), and the mixture was submitted to the hydrogenating reaction at ambient temperature under ambient pressure. After completion of the reaction, catalyst was filtered off using celite and then solvent was distilled off. Acetic anhydride (50 ml) was added to the residue obtained and the mixture was stirred for 1 hour at room temperature. The reaction mixture was poured into ice water and neutralized with sodium carbonate. Then, the precipitated crystals were collected by filtration, washed with water and then air-dried, thereby obtaining 19.4 g of title compound as colorless powder. Yield 80%.

1H-NMR(DMSO-d6, δ): 2.10(3H,s), 2.30(3H,s), 7.39 (1H,d,J=8.3 Hz), 7.44(1H,d,J=8.3 Hz), 7.89(1H,s), 9.46(1H, s).

Referential Example 12

2-Methyl-4-nitro-5-trifluoromethylacetanilide

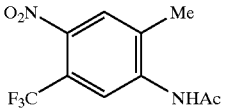

Using the compound of Referential example 11 (19.4 g, 89.3 mmol) and through the process similar to Referential example 1, 9.77 g of title compound were obtained as colorless powder. Yield 42%.

1H-NMR(DMSO-d6, δ): 2.18(3H,s), 2.40(3H,s), 8.11 (1H,s), 8.39(1H,d, s), 9.74(1H,s).

Referential Example 13

5-Nitro-4-trifluoromethylanthranilic acid

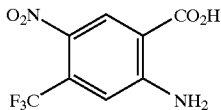

To a suspension of the compound of Referential example 12 (9.70 g, 37.0 mmol) in water (200 ml) was added little by little a mixture of potassium permanganate (35.1 g, 222 mmol) and magnesium sulfate (13.4 g, 111 mmol) at 100° C., and the mixture was refluxed until potassium permanganate faded out. After cooling, the insolubles were filtered off using celite and the pH value was brought to 9 using sodium carbonate, which was washed with ethyl acetate. The aqueous layer was brought to pH1 using concentrated hydrochloric acid, which was extracted with ethyl acetate, dried over anhydrous sodium sulfate, and then solvent was distilled off. To the residue obtained was added 4 mol/L hydrochloric acid (100 ml), and the mixture was refluxed for 3 hours. After cooling, this was extracted with ethyl acetate, dried over anhydrous sodium sulfate, and then solvent was distilled off, thereby obtaining 2.09 g of title compound as yellowish white powder. Yield 23%.

1H-NMR(DMSO-d6, δ): 7.36(1H,s), 8.06(2H,brs), 8.58 (1H,s).

Referential Example 14

5-Nitro-4-trifluoromethylanthranilaldehyde

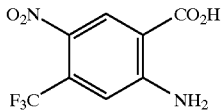

Using the compound of Referential example 13 (1.00 g, 4.00 mmol) and through the process similar to Referential example 4, 244 mg of title compound were obtained as yellow powder. Yield 26%.

1H-NMR(CDCl$_3$, δ): 7.09(1H,s), 8.45(1H,s), 9.97(1H,s).

Referential Example 15

Ethyl 1,2-dihydro-6-nitro-2-oxo-7-trifluoromethylquinoline-3-carboxylate

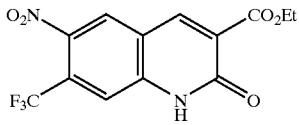

Using the compound of Referential example 14 (186 mg, 794 μmol) and through the process similar to Referential example 5, 121 mg of title compound were obtained as pale yellow powder. Yield 46%.

1H-NMR(DMSO-d6, δ): 1.31(3H,t,J=6.8 Hz), 4.31(2H, q,J=6.9 Hz), 7.80 (1H,s), 8.67(1H,s), 8.84(1H,s), 12.50–13.00(1H,br).

Referential Example 16

Ethyl 6-amino-1,2-dihydro-2-oxo-7-trifluoromethylquinoline-3-carboxylate

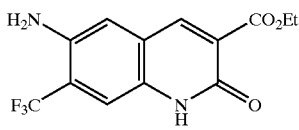

To a solution of the compound of Referential example 15 (224 mg, 678 μmol) in ethanol (10 ml) was added 10% palladium-carbon (20.0 mg), and the mixture was stirred at room temperature under hydrogen atmosphere. After completion of the reaction, the precipitated crystals were dissolved by adding N,N-dimethylformamide, then catalyst was filtered off using celite, and solvent was distilled off. Ethyl acetate was added to the residue obtained. The crystals were collected by filtration, washed with ethyl acetate and then air-dried, thereby obtaining 197 mg of title compound as yellow powder. Yield 97%.

1H-NMR(DMSO-d6, δ): 1.30(3H,t,J=7.3 Hz), 4.27(2H, q,J=7.3 Hz), 5.45(2H,s), 7.15(1H,s), 7.40(1H,s), 8.25(1H,s), 11.82(1H,s).

Biological Activity

Binding Experiment Against AMPA Receptor

To a crude synaptic membranes preparation prepared from cerebral cortex in rat were added [$^3$H]-AMPA (final concentration: 5 nmol/L) that binds selectively to AMPA receptors, potassium thiocyanate (final concentration: 100 mmol/L) and testing compound, and the mixture was incubated for 30 minutes at 0° C. After the reaction was stopped by suction filtration, the radioactivity on filter was measured with liquid scintillation counter. The specific binding level of [$^3$H]-AMPA was determined by subtracting the non-specific binding level in the presence of glutamic acid (0.1 mmol/L) from total binding level. The [$^3$H]-AMPA binding in the absence of testing compound was put on 100, and the concentration of compound to decrease by 50% (IC$_{50}$ value) was determined, which was converted to Ki value to calculate the binding capacity of each compound to AMPA receptor (Eur. J. Pharmacol., 1993, 246, 195–204).

Activity table-A

| Testing compound | Y | U | W | [$^3$H]-AMPA (Ki: nmol/L) |
|---|---|---|---|---|
| Example 2 | N | O | Ph | 22.4 |
| Example 6 | N | O | 2-F-Ph | 8.22 |
| Example 15 | N | O | 3-CO2H-Ph | 17.8 |
| Example 16 | N | O | 4-CO2H-Ph | 16.5 |

Activity table-B

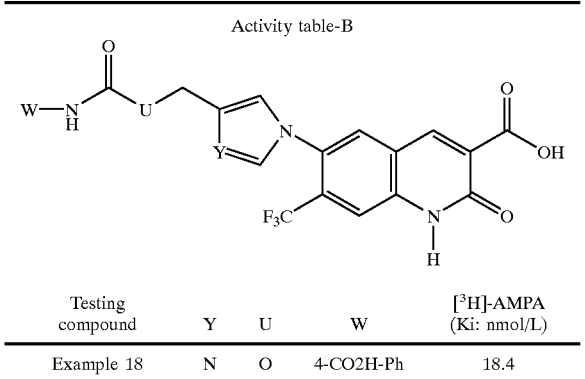

| Testing compound | Y | U | W | [³H]-AMPA (Ki: nmol/L) |
|---|---|---|---|---|
| Example 18 | N | O | 4-CO2H-Ph | 18.4 |

RESULT

From the results above, the 6-substituted heteroquinolinecarboxylic acid derivatives of the invention are novel compounds with excellent antagonism against excitatory amino acid receptors, in particular, AMPA receptor in non-NMDA receptor.

Since these inventive compounds inhibit the binding of excitatory amino acid receptor that causes the death of nerve cells to AMPA receptor, they are effective for the therapies of disorder of cerebral nerve cells due to excitatory amino acid aforementioned, etc., and can be said to be useful compounds expressing no adverse effects that the drugs with antagonism against NMDA receptor have.

What is claimed is:

1. 6-Substituted heteroquinolinecarboxylic acid derivatives and addition salts thereof represented by formula (1)

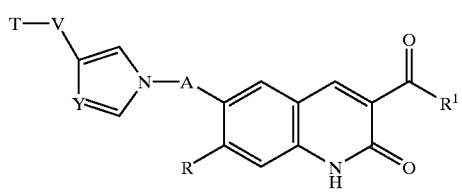

(1)

wherein
A denotes a single bond or methylene (CH2),
Y denotes a nitrogen atom or =CH—,
V denotes a single bond or methylene (CH2),
T denotes a hydroxyl group, amino group, lower alkoxycarbonyl group, carboxyl group, aldehyde group, or formula (2)

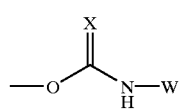

(2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, a cycloalkyl group, or formula (3)

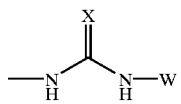

(3)

wherein
X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group,
R denotes a nitro group, trifluoromethyl group or halogen atom, and
R¹ denotes a hydroxyl group or lower alkoxy group.

2. 6-Substituted heteroquinolinecarboxylic acid derivatives and addition salts thereof of claim 1, represented by formula (1)

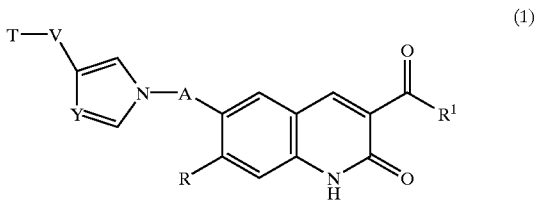

(1)

wherein
A denotes a single bond,
Y denotes a nitrogen atom or =CH—,
V denotes a methylene (CH₂),
T denotes a general formula (2)

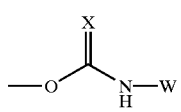

(2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, a cycloalkyl group, or formula (3)

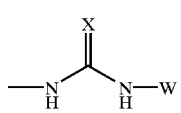

(3)

wherein
X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, R denotes a nitro group, trifluoromethyl group or halogen atom, and R¹ denotes a hydroxyl group or lower alkoxy group.

3. A process for preparing the 6-substituted heteroquinolinecarboxylic acid derivatives and their addition salts of claim 1, comprising hydrolyzing compounds represented by formula (4)

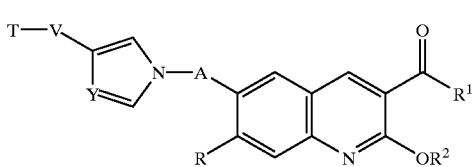

(4)

wherein

A denotes a single bond or methylene (CH₂),

Y denotes a nitrogen atom or =CH—,

V denotes a single bond or methylene (CH₂),

T denotes a hydroxyl group, amino group, lower alkoxycarbonyl group, carboxyl group, aldehyde group, or formula (2)

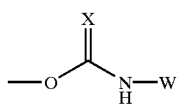

(2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, a cycloalkyl group, or formula (3)

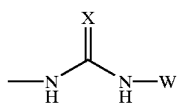

(3)

wherein

X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, R denotes a nitro group, trifluoromethyl group or halogen atom, R¹ denotes a hydroxyl group or lower alkoxy group, and R² denotes a lower alkyl group which may be substituted with halogen atom, or an aralkyl group which may have one or more substituents.

4. A process for preparing the 6-substituted heteroquinolinecarboxylic acid derivatives and their addition salts of claim 1, wherein, Y represents =CH—, comprising reacting compounds represented by formula (5)

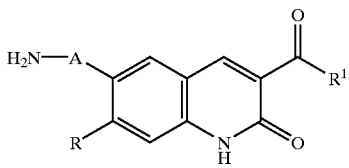

(5)

wherein

A denotes a single bond or methylene (CH₂),

R denotes a nitro group, trifluoromethyl group or halogen atom, and

R¹ denotes a hydroxyl group or lower alkoxy group, with compounds represented by formula (6)

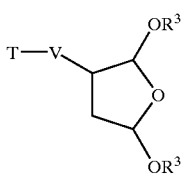

(6)

wherein

V denotes a single bond or methylene (CH₂),

T denotes a hydroxyl group, amino group, lower alkoxycarbonyl group, carboxyl group, aldehyde group, or formula (2)

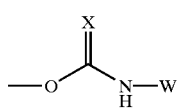

(2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, a cycloalkyl group, or formula (3)

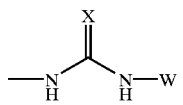

(3)

wherein

X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, and R³ denotes a lower alkyl group which may be substituted with a halogen atom, or an aralkyl group which may have one or more substituents.

5. A process for preparing the 6-substituted heteroquinolinecarboxylic acid derivatives and their addition salts of claim 1, wherein T represents formula (2) or formula (3), comprising reacting compounds represented by formula (7)

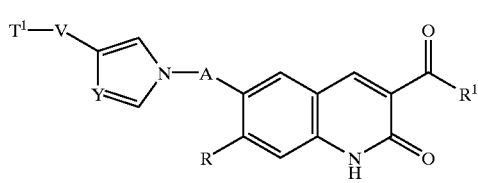

(7)

wherein

A denotes a single bond or methylene (CH$_2$),

Y denotes a nitrogen atom or =CH—,

V denotes a single bond or methylene (CH2),

T$^1$ denotes a hydroxyl group or amino group,

R denotes a nitro group, trifluoromethyl group or halogen atom, and

R$^1$ denotes a hydroxyl group or lower alkoxy group, with isocyanic or isothiocyanic esters represented by formula (8)

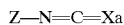

Z—N=C=Xa     (8)

wherein

Z denotes an aralkyl group, phenyl group, naphthyl group, 5- or 6-membered heterocycle and its condensed ring each of which may be optionally substituted with one or more substituents on the aromatic ring or heterocycle ring, a lower alkyl group which may be substituted with a halogen atom, or a cycloalkyl group, and Xa denotes an oxygen atom or sulfur atom, or with isocyanic or isothiocyanic esters synthesized from precursors of isocyanic or isothiocyanic esters represented by formula (9)

Z—A$_1$—D     (9)

wherein Z denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, A$_1$ denotes a single bond, and D denotes an amino group, carboxyl group, amide group or lower alkoxycarbonyl group.

6. Synthetic intermediates represented by formula (4)

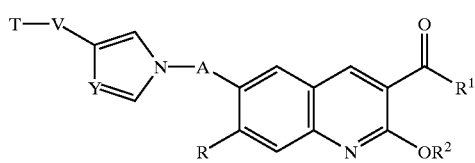

(4)

wherein

A denotes a single bond or methylene (CH$_2$),

Y denotes a nitrogen atom or =CH—,

V denotes a single bond or methylene (CH$_2$),

T denotes a hydroxyl group, amino group, lower alkoxycarbonyl group, carboxyl group, aldehyde group, or formula (2)

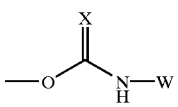

(2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, a cycloalkyl group, or formula (3)

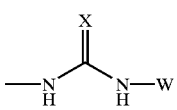

(3)

wherein

X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, R denotes a nitro group, trifluoromethyl group or halogen atom, R$^1$ denotes a hydroxyl group or lower alkoxy group, and R$^2$ denotes a lower alkyl group which may be substituted with a halogen atom, or an aralkyl group which may have one or more substituents.

7. A process for preparing the synthetic intermediates of claim 6, comprising reacting compounds represented by a general formula (10)

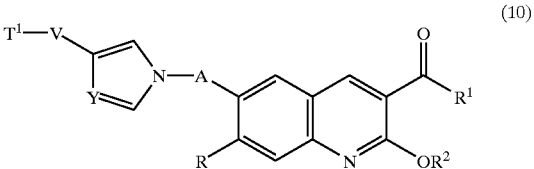

(10)

wherein

A denotes a single bond or methylene (CH$_2$),

Y denotes a nitrogen atom or =CH—,

V denotes a single bond or methylene (CH$_2$),

T$_1$ denotes a hydroxyl group or amino group,

R denotes a nitro group, trifluoromethyl group or halogen atom,

R$^1$ denotes a hydroxyl group or lower alkoxy group, and

R$^2$ denotes a lower alkyl group which may be substituted with halogen atom, or an aralkyl group which may have one or more substituents, with isocyanic or isothiocyanic esters represented by formula (8)

Z—N=C=Xa     (8)

wherein

Z denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, and Xa denotes an oxygen atom or sulfur atom, or with isocyanic or isothiocyanic esters synthesized from precursors of isocyanic or isothiocyanic esters represented by formula (9)

 (9)

wherein Z denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, $A_1$ denotes a single bond, and D denotes an amino group, carboxyl group, amide group or lower alkoxycarbonyl group.

8. A process for preparing the compounds of claim 6, comprising reacting compounds represented by formula (11)

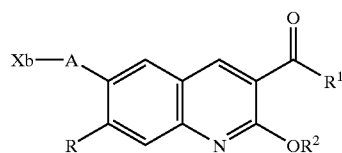 (11)

wherein
A denotes a single bond or methylene ($CH_2$),
Xb denotes a halogen atom,
R denotes a nitro group, trifluoromethyl group or halogen atom,
$R^1$ denotes a hydroxyl group or lower alkoxy group, and
$R^2$ denotes a lower alkyl group which may be substituted with a halogen atom, or an aralkyl group which may have one or more substituents,
with compounds represented by formula (12)

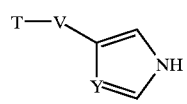 (12)

wherein
Y denotes a nitrogen atom or =CH—,
V denotes a single bond or methylene ($CH_2$),
T denotes a hydroxyl group, amino group, lower alkoxycarbonyl group, carboxyl group, aldehyde group, or formula (2)

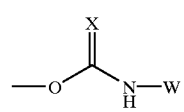 (2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, a cycloalkyl group, or formula (3)

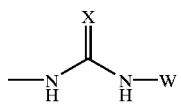 (3)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group.

9. A composition comprising as effective ingredients one or more 6-substituted heteroquinolinecarboxylic acid derivatives and their addition salts represented by formula (1)

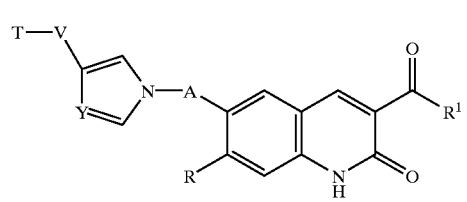 (1)

wherein
A denotes a single bond or methylene ($CH_2$),
Y denotes a nitrogen atom or =CH—,
V denotes a single bond or methylene ($CH_2$),
T denotes a hydroxyl group, amino group, lower alkoxycarbonyl group, carboxyl group, aldehyde group, or formula (2)

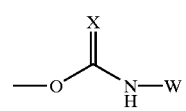 (2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, a cycloalkyl group, or formula (3)

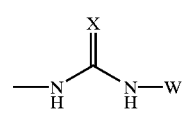 (3)

wherein
X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group,
R denotes a nitro group, trifluoromethyl group or halogen atom, and
$R^1$ denotes a hydroxyl group or lower alkoxy group.

10. A composition comprising as effective ingredients one or more 6-substituted heteroquinolinecarboxylic acid derivatives and their addition salts represented by formula (1)

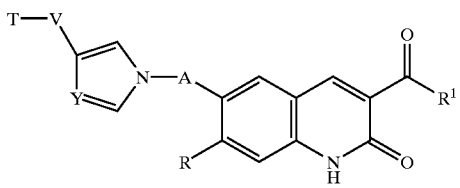 (1)

wherein
 A denotes a single bond,
 Y denotes a nitrogen atom or =CH—,
 V denotes a methylene (CH$_2$),
 T denotes formula (2)

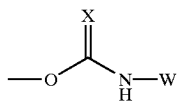 (2)

wherein X denotes an oxygen atom or sulfur atom, W denotes an aralkyl group, phenyl group, naphthyl group, 5- or 6-membered heterocycle and its condensed ring each of which may be optionally substituted with one or more substituents on the aromatic ring or heterocycle ring, a lower alkyl group which may be substituted with a halogen atom, a cycloalkyl group, or formula (3)

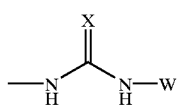 (3)

wherein
 X denotes an oxygen atom or sulfur atom, W denotes an aralkyl group, phenyl group, naphthyl group, 5- or 6-membered heterocycle and its condensed ring each of which may be optionally substituted with one or more substituents on the aromatic or heterocycle ring, a lower alkyl group which may be substituted with a halogen atom, or a cycloalkyl group, R denotes a nitro group, trifluoromethyl group or halogen atom, and R$^1$ denotes a hydroxyl group or lower alkoxy group.

11. A method of inhibiting the interaction of an excitatory amino acid receptor with an excitatory amino acid comprising contacting the excitatory amino acid receptor with an amount of the 6-substituted heteroquinolinecarboxylic acid derivatives of claim 1 sufficient to inhibit said interaction.

12. The method of claim 11, wherein the excitatory amino acid receptor is a non-NMDA receptor.

13. The method of claim 11, wherein the excitatory amino acid receptor is a AMPA receptor.

14. A method of inhibiting the interaction of an excitatory amino acid receptor with an excitatory amino acid comprising contacting the excitatory amino acid receptor with an amount of the 6-substituted heteroquinolinecarboxylic acid derivatives of claim 2 sufficient to inhibit said interaction.

15. A method of inhibiting the interaction of an excitatory amino acid receptor with an excitatory amino acid comprising contacting the excitatory amino acid receptor with an amount of the composition of claim 9 sufficient to inhibit said interaction.

16. A method of inhibiting the interaction of an excitatory amino acid receptor with an excitatory amino acid comprising contacting the excitatory amino acid receptor with an amount of the composition of claim 10 sufficient to inhibit said interaction.

17. The method of claim 11, wherein said receptor is on the surface of a cell.

18. The method of claim 17, wherein said cell is a neural cell.

19. The method of claim 18, wherein said cell is in a patient suffering from a cerebral hemorrhage, head trauma, epilepsy, Huntington's disease, Parkinson's disease, amyotrophic lateral sclerosis, and Alzheimer's disease.

20. A method of treating a condition selected from the group consisting of cerebral hemorrhage, head trauma, epilepsy, Huntington's disease, Parkinson's disease, amyotrophic lateral sclerosis, and Alzheimer's disease, comprising administering a 6-substituted heteroquinolinecarboxylic acid derivative of claim 1 to a patient having the condition, in an amount effective to inhibit the interaction of an excitatory amino acid receptor with an excitatory amino acid.

* * * * *